US009027382B2

(12) United States Patent
Naruishi

(10) Patent No.: US 9,027,382 B2
(45) Date of Patent: May 12, 2015

(54) CASE FOR IMPACT DETECTOR, IMPACT DETECTOR, AND PACKAGE

(71) Applicant: Moku Naruishi, Kanagawa (JP)

(72) Inventor: Moku Naruishi, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 103 days.

(21) Appl. No.: 13/964,318

(22) Filed: Aug. 12, 2013

(65) Prior Publication Data

US 2014/0047897 A1  Feb. 20, 2014

(30) Foreign Application Priority Data

Aug. 17, 2012 (JP) .................. 2012-181224
May 31, 2013 (JP) .................. 2013-115094

(51) Int. Cl.
*G01N 3/30* (2006.01)
*G01C 9/10* (2006.01)
*G01D 11/24* (2006.01)
*G01P 1/12* (2006.01)
*G01P 15/03* (2006.01)
*G01P 15/18* (2013.01)

(52) U.S. Cl.
CPC ...... *G01N 3/30* (2013.01); *G01P 1/127* (2013.01); *G01P 15/032* (2013.01); *G01P 15/18* (2013.01); *G01P 15/036* (2013.01); *G01C 9/10* (2013.01); *G01D 11/245* (2013.01)

(58) Field of Classification Search
CPC ..... G01P 15/036; G01P 15/18; G01P 15/032; G01P 1/127; G01C 9/10; G01N 3/30; G01D 11/245
USPC .................. 73/12.01, 12.06, 12.13
See application file for complete search history.

(56) References Cited

U.S. PATENT DOCUMENTS

| | | | | |
|---|---|---|---|---|
| 8,074,489 B2 * | 12/2011 | Ishikawa et al. | ............. | 73/12.04 |
| 8,234,993 B2 * | 8/2012 | Naruishi et al. | ............. | 116/203 |
| 8,234,994 B1 * | 8/2012 | Branch | ................. | 116/203 |
| 8,240,270 B2 * | 8/2012 | Naruishi | ................. | 116/203 |
| 8,307,775 B2 * | 11/2012 | Naruishi et al. | ............. | 116/203 |
| 8,493,225 B2 * | 7/2013 | Naruishi et al. | ............. | 340/665 |

(Continued)

FOREIGN PATENT DOCUMENTS

| | | |
|---|---|---|
| DE | 196 05 041 A1 | 8/1997 |
| JP | 2009-156726 | 7/2009 |
| WO | WO 00/37889 | 6/2000 |

OTHER PUBLICATIONS

The Extended European Search Report issued Oct. 22, 2013, in Application No. / Patent No. 13180177.1-1558.

*Primary Examiner* — Freddie Kirkland, III
(74) *Attorney, Agent, or Firm* — Oblon, McClelland, Maier & Neustadt, L.L.P.

(57) ABSTRACT

The present invention provides a case for an impact detector, including: a front case; a weight to move from an initial position when a detection target of the impact detector inclines more than a predetermined angle; a first rear case to be covered by the front case, including a guide member set at a first inclination angle, through which the weight moves; a second rear case to be covered by the front case, including a guide member set at a second inclination angle different from the first inclination angle, through which the weight moves; and a resistance reducer to reduce moving resistance of the weight. In the optimal case for the impact detector, the front case is used in common for the first rear case and the second rear case, the weight can move smoothly in either case, and the impact can be easily detected.

7 Claims, 35 Drawing Sheets

(56) References Cited

U.S. PATENT DOCUMENTS

| | | |
|---|---|---|
| 2010/0050733 A1 | 3/2010 | Naruishi |
| 2010/0281946 A1 | 11/2010 | Naruishi et al. |
| 2010/0300178 A1 | 12/2010 | Naruishi et al. |
| 2011/0090090 A1 | 4/2011 | Naruishi et al. |
| 2014/0069837 A1* | 3/2014 | Naruishi et al. ........... 206/459.1 |
| 2014/0071275 A1* | 3/2014 | Kawase et al. ................ 348/143 |

* cited by examiner

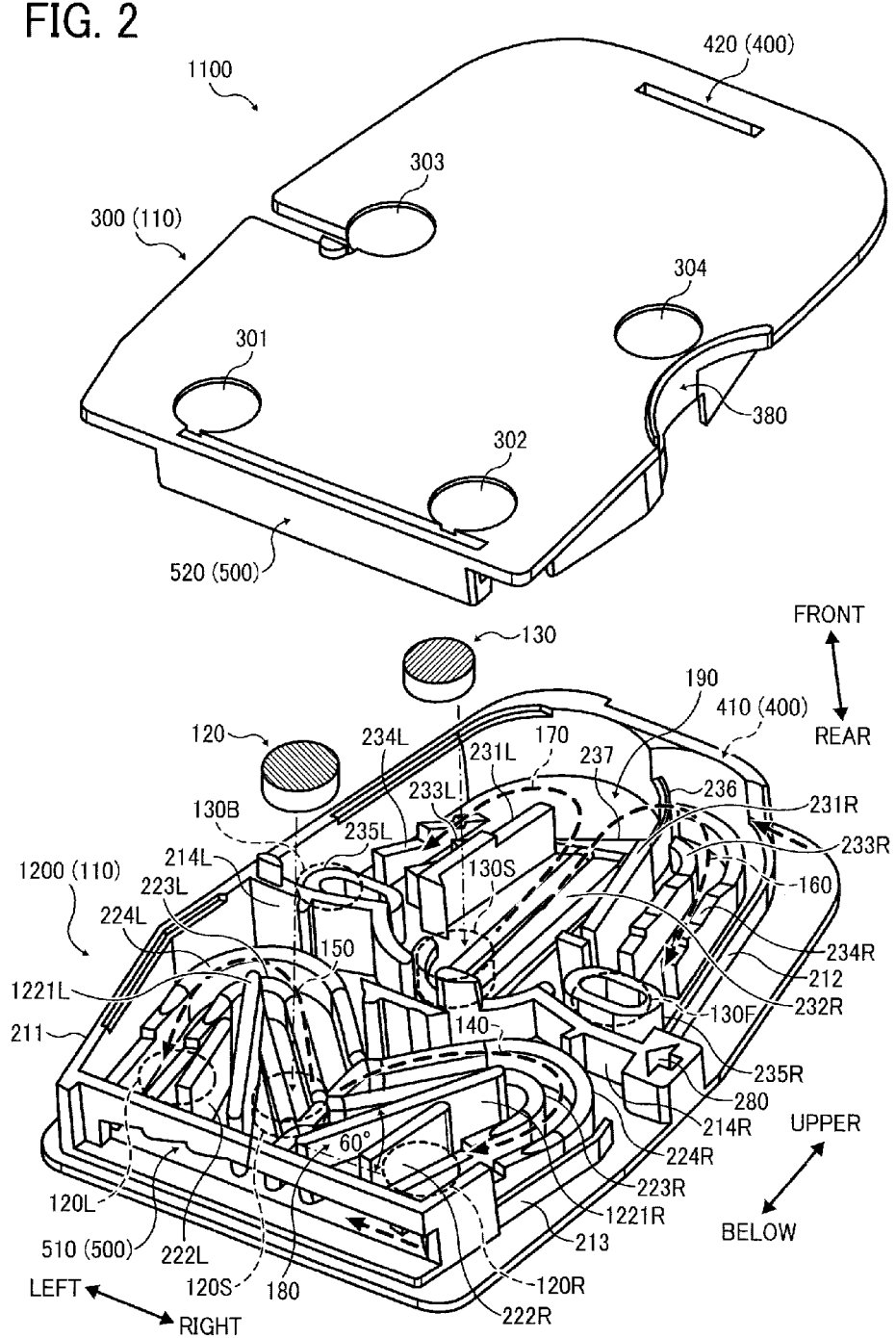

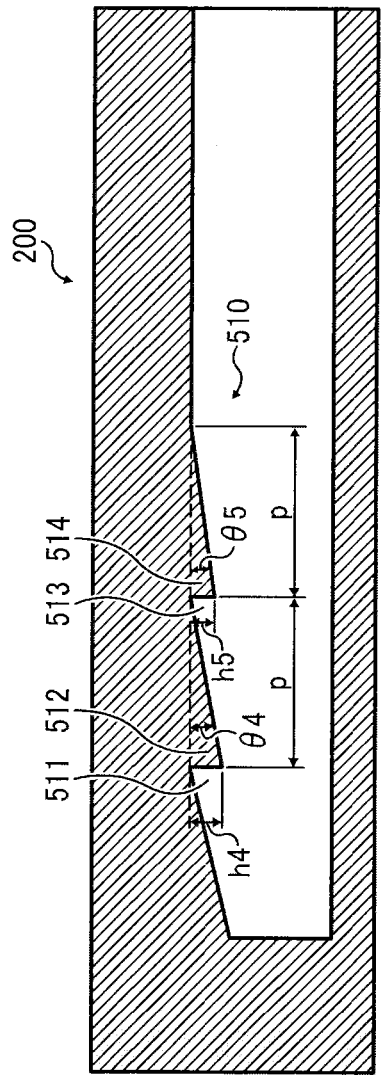
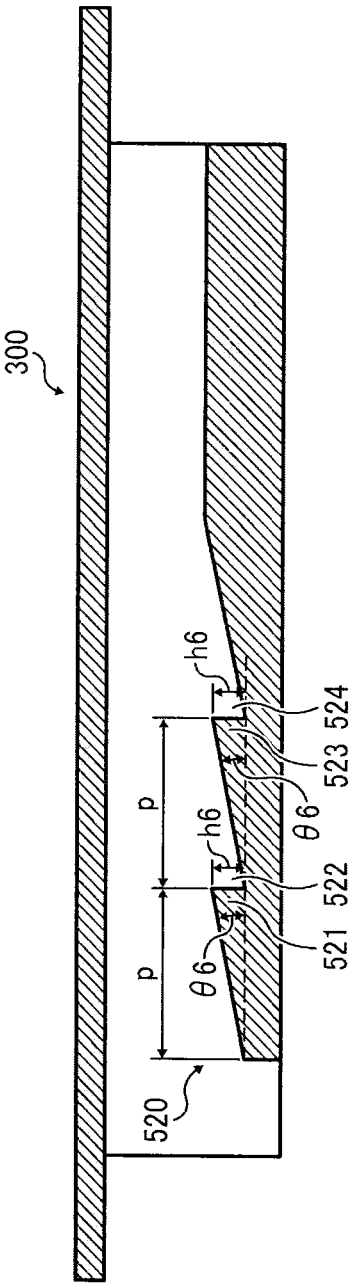

INITIAL POSITION

SLANTED RIGHTWARD

SLANTED LEFTWARD

INITIAL POSITION

SLANTED RIGHTWARD

SLANTED LEFTWARD

INITIAL POSITION

SLANTED REARWARD

SLANTED FRONTWARD

CASE FOR IMPACT DETECTOR, IMPACT DETECTOR, AND PACKAGE

CROSS-REFERENCE TO RELATED APPLICATION

The present application claims priority pursuant to 35 U.S.C. §119 from Japanese patent application numbers 2012-181224 and 2013-115094, filed on Aug. 17, 2012 and May 31, 2013, respectively, the entire disclosures of which are incorporated by reference herein.

BACKGROUND

1. Technical Field

The present invention relates to a case for an impact detector to detect that a product has received an impact or a forth, and further relates to an impact detector using the case, and a package employing the impact detector.

2. Related Art

When a product such as a precision device is transported, there is an occasion where the product is damaged due to handling in the transportation. If the impact or the forth given to the product is below a certain level, a damage preventive measure taken during packaging may prevent damage to the product. However, when unexpected shock or force has been applied to the product due to erroneous or rough handling, damage to the product cannot be prevented completely.

If the exterior package is greatly damaged due to the impact, damage to the internal product can be found before arriving at a customer's site or a store. However, there is a case in which an internal product only is damaged even though there is no change in the external appearance. In such a case, the damage to the product is found after the customer has received the product and unpacked it, which may cause claims from the customer and a loss of reliability to the vendor. Then, an approach has been taken, in which a package is provided with an impact detector and the impact applied to the package is detected.

JP-2009-156726-A discloses an impact detector, in which a weight is provided in a case formed of a front case and a rear case and the weight moves in the paths when the package is tilted beyond a certain angle, which is observed from a window disposed on the front case.

The impact detector as disclosed in JP-2009-156726-A is configured to detect the impact for the first time when the tilt angle exceeds a previously set angle and the set angle cannot be changed. However, the tilt angle allowable for the packaged product is different for each type of product, so that the impact detector needs to cope with different tilt angles.

Such an impact detector includes at least two case members and includes a weight disposed in the case members. Then, each case needs to be formed corresponding to the slant to detect at least one of the cases.

SUMMARY

Considering the above point, the present invention provides a commonly useable case member for the impact detector which detects at least two types of tilt angles, in which weights can move smoothly even when detecting either of the tilt angles.

More specifically, the present invention provides a case for an impact detector, including: a front case; a weight to move from an initial position when a detection target of the impact detector inclines more than a predetermined angle; a first rear case to be covered by the front case, including a guide member set at a first inclination angle, through which the weight moves; a second rear case to be covered by the front case, including a guide member set at a second inclination angle different from the first inclination angle, through which the weight moves; and a resistance reducer to reduce moving resistance of the weight. In the optimal case for the impact detector, the front case is used in common for the first and second rear cases; the resistance reducer includes a first resistance reducer disposed at a same angle with the guide member of the first rear case and a second resistance reducer disposed apart from the first resistance reducer; the weight contacts the second resistance reducer when the front case is attached to the first rear case member; and the weight contacts the first and second reducers when the front case is attached to the second rear case member.

These and other objects, features, and advantages of the present invention will become apparent upon consideration of the following description of the preferred embodiments of the present invention when taken in conjunction with the accompanying drawings.

BRIEF DESCRIPTION OF THE DRAWINGS

FIG. 2 is an exploded perspective view of an impact detector related to the first embodiment of the present invention when a second rear case member is used;

FIGS. 3A and 3B each show an assembly of the impact detector according to the first embodiment, in which FIG. 3A is a plan view showing a state in which the front case member covers the second rear case member, and FIG. 3B is a plan view showing a first combination position by the front case member and the second rear case member;

FIGS. 5A and 5B are an upper-side detention device of the impact detector according to the first embodiment along Line C-C in FIG. 4, of which FIG. 5A is an end view of the rear case member and FIG. 5B is an end view of the front case member;

FIGS. 6A to 6C show operations of the upper-side detention device as illustrated in FIGS. 5A and 5B, of which FIG. 6A is an end view showing a state in which the front case member covers the first rear case member; FIG. 6B is an end view showing the first combination position; and FIG. 6C is an end view showing the second combination position;

FIGS. 7A and 7B show states of the lower-side detention device of the impact detector according to the first embodiment along Line D-D in FIG. 4, of which FIG. 7A is an end view of the rear case member and FIG. 7B is an end view of the front case member;

FIGS. 8A to 8C show operations of the lower-side detention device as illustrated in FIGS. 7A and 7B, of which FIG. 8A is an end view showing a state in which the front case member covers the first rear case member; FIG. 8B is an end view showing the first combination position thereof; and FIG. 8C is an end view showing the second combination position thereof;

FIGS. 9A and 9B show a moving range of the weight according to a switching means of the impact detector according to the first embodiment, of which FIG. 9A is a plan view showing the first combination position, and FIG. 9B is a plan view showing the second combination position;

FIGS. 13A and 13B each show the first rear case member of the impact detector, of which FIG. 13A shows a plan view and FIG. 13B shows a bottom view thereof;

FIGS. 14A and 14B each show the first rear case member of the impact detector, of which FIG. 14A shows a perspective view of the same and FIG. 14B shows a perspective view seen from another direction;

FIGS. 15A and 15B each show the second rear case member of the impact detector according to the first embodiment, of which FIG. 15A shows a plan view and FIG. 15B shows a bottom view thereof;

FIGS. 16A and 16B each show the second rear case member of the impact detector, of which FIG. 15A shows a perspective view of the same and FIG. 15B shows a perspective view seen from another direction;

FIGS. 17A and 17B each show the front case of the impact detector, of which FIG. 17A shows a plan view and FIG. 17B shows a bottom view thereof;

FIGS. 18A and 18B each show the front case of the impact detector, of which FIG. 18A shows a perspective view of the same and FIG. 18B shows a perspective view seen from another direction;

FIGS. 19A and 19B each show a contacting state between the rails of the front case and the weight, of which FIG. 19A shows a schematic view using the first rear case member, and FIG. 19B shows a schematic view using the second rear case member;

FIGS. 23A and 23B each show a cross-sectional view of the first impact detector along the Line B-B in FIG. 3B, of which FIG. 23A shows a cross-sectional view when the first impact detector falls in the distal direction, and FIG. 23B shows a cross-sectional view when the first impact detector falls in the proximal direction;

DETAILED DESCRIPTION

Hereinafter, a schematic configuration of an impact detector related to a first embodiment will be described.

In the first embodiment, two types of impact detectors are provided: one is formed of a front case member 300, a common case member, and a first rear case member 200; and the other formed of the common front case member 300 and a second rear case member 1200. The two types of impact detectors each come into a detecting state at a different tilt angle. Specifically, a first impact detector 100 is formed by combining the front case member 300 with the first rear case member 200, and a second impact detector 1100 is formed by combining the front case member 300 with the second rear case member 1200. The first impact detector 100 comes into the detecting state when inclined by 45 degrees, and the second impact detector 1100 comes into the detecting state when inclined by 60 degrees. In addition, the impact detectors 100, 1100 according to the first embodiment employ the front case member 300 as a common case member used for both impact detectors 100, 1100 handling with different inclinations; however, the common case member may be configured by the rear case member alone.

Figure 1:
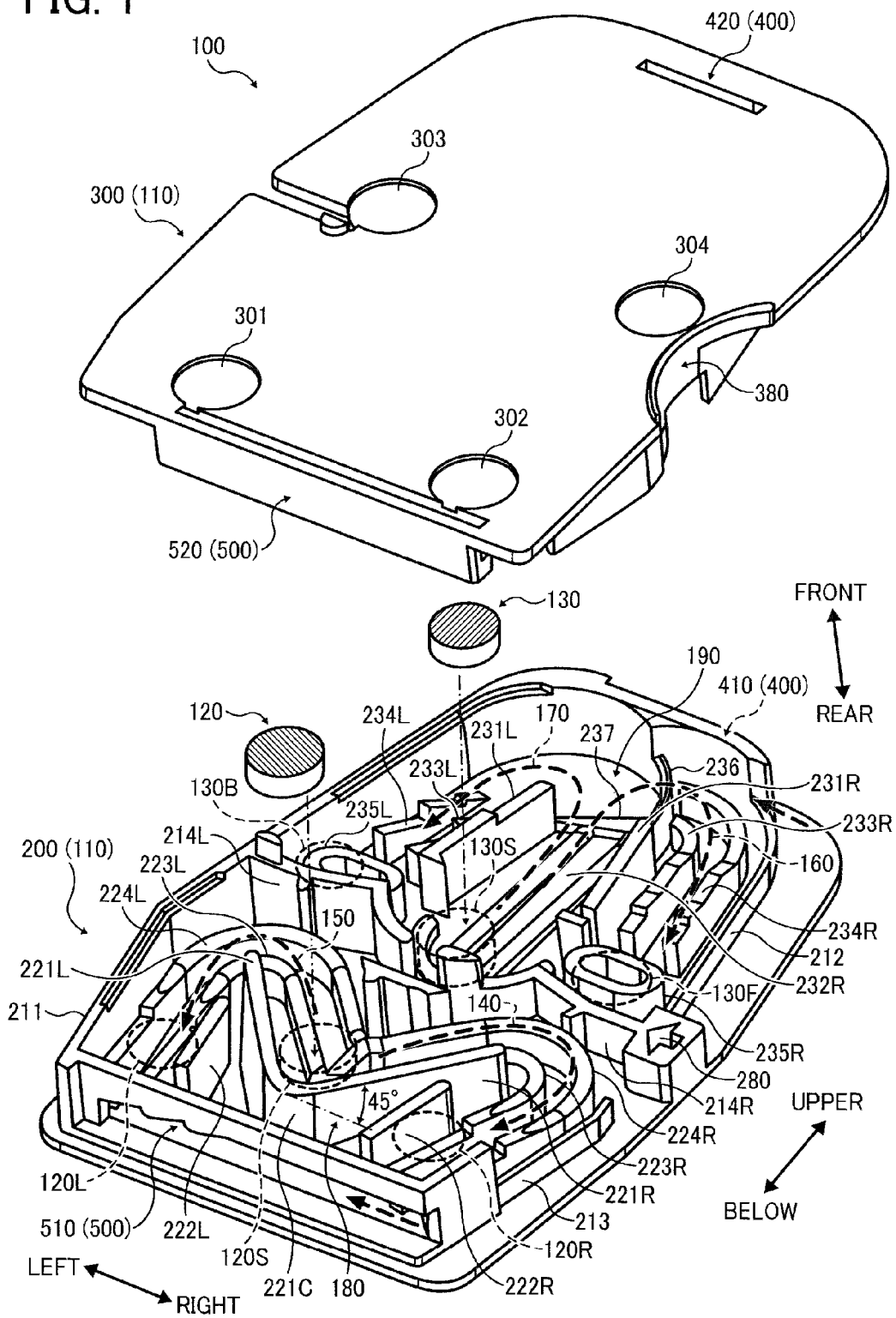
FIG. 1 is an exploded perspective view of an impact detector related to a first embodiment of the present invention when a first rear case member is used.

FIG. 1 is an exploded perspective view of an impact detector related to the first embodiment of the present invention when the first rear case member is used. The impact detector 100 includes a lateral direction sensor section 180 detecting that a drop or tilt has occurred in the horizontal direction in the case 110; and a front-back direction sensor section 190 detecting that a drop or tilt has occurred in the front-back direction in the case 110.

In addition, the first impact detector 100 further includes two discoidal weights including a first weight 120 and a second weight 130 in the case 110. The first weight 120 is disposed at the lateral direction sensor section 180 and the second weight 130 at the front-back direction sensor section 190.

The lateral direction sensor section 180 includes a right-side weight path 140 and a left-side weight path 150 to guide the first weight 120. The right-side weight path 140 guides the first weight 120 from an initial position 120S to a right-side detection position 120R. The right-side weight path 150 guides the first weight 120 from the initial position 120S to a left-side detection position 120L. The right-side weight path 140 and the left-side weight path 150 are formed such that the first weight 120 moves when the first impact detector 100 is tilted by 45 degrees.

The front-back direction sensor section 190 includes a proximal weight path 160 and a distal weight path 170 to guide the second weight 130. The proximal weight path 160 guides the second weight 130 from an initial position 130S to a proximal detection position 130F. In addition, the proximal weight path 160 guides the second weight 130 from the initial position 130S to a distal detection position 130B.

The first impact detector 100 includes the front-back direction sensor section 190 disposed above the lateral direction sensor section 180. In place of the front-back direction sensor section 190, various other forms of weight can be employed by combining any of the various forms. For example, the one in which the weight held by an elastic member falls by being separated from the elastic member due to the impact may be used. Further, the first impact detector 100 may include only the lateral direction sensor section 180.

The first rear case member 200 is a mold of synthetic resins such as opaque ABS resins of black color, for example, and includes projections of various shapes to form, in combination with the front case member 300, the right-side weight path 140, the left-side weight path 150, the proximal weight path 160, and the distal weight path 170. Further, the front case member 300 is a mold of synthetic resins such as transparent ABS resins, and includes projections of various shapes to form, in combination with the first rear case member 200, the right-side weight path 140, the left-side weight path 150, the proximal weight path 160, and the distal weight path 170.

In addition, the front case member 300 includes a top plate 310 that includes observation windows 301, 302, 303, and 304. The weights 120, 130 which have moved to each detection position in each of the weight paths can be observed from the observation windows 301, 302, 303, and 304. The observation windows 301, 302, 303, and 304 each may include a convex lens for optimal visibility.

The first weight 120 and the second weight 130 are preferably formed of a material with a comparatively high specific gravity. Even with a smaller thickness and diameter, the mass may be adjusted and the impact detector 100 can be made compact. Preferred materials for the first weight 120 and the second weight 130 are corrosion-resistant stainless steel and aluminum. The periphery of the weight should be chamfered so that the weight can move smoothly in the case 110. Further, it is preferred that each weight is colored with a different color or has a different label for an easier discrimination.

Next, the second impact detector 1100 will be described.

FIG. 2 is an exploded perspective view of an impact detector according to the first embodiment when the second rear case member is used. The second impact detector 1100 is formed by combining the second rear case member 1200 and the front case member 300. The same front case member 300 used in the first impact detector 100 can be used. In the second rear case member 1200, the right-side weight path 140 and the left-side weight path 150 are configured such that the first weight 120 moves when the second impact detector 1100 is tilted by 60 degrees. As a result, as will be described later, the part that forms the right-side weight path 140 and the left-side weight path 150 is different from the first rear case member 200.

Next, how to assemble the impact detector will be described. Because the first impact detector 100 and the second impact detector 1100 are assembled in a similar manner, assembly of only one of the first rear case member 200 and the second rear case member 1200 is described, it being understood that the description applies equally to both case members.

Figure 3A:
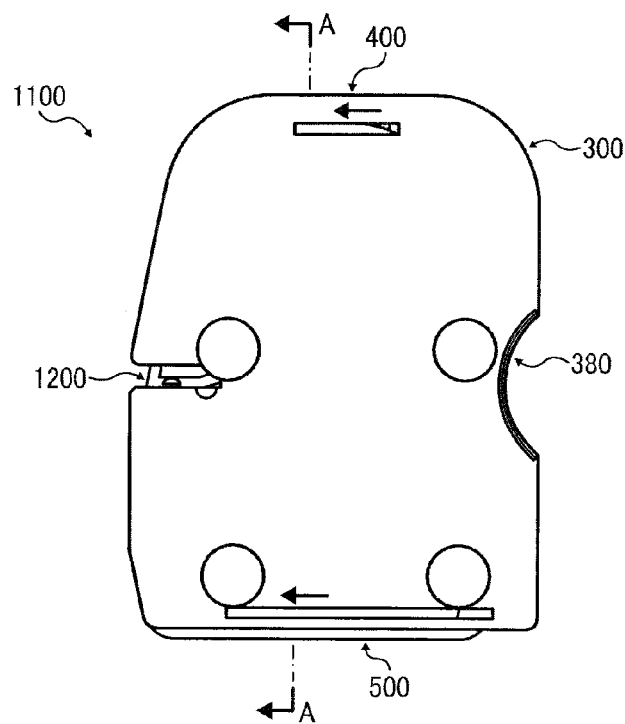
Figure 3B:
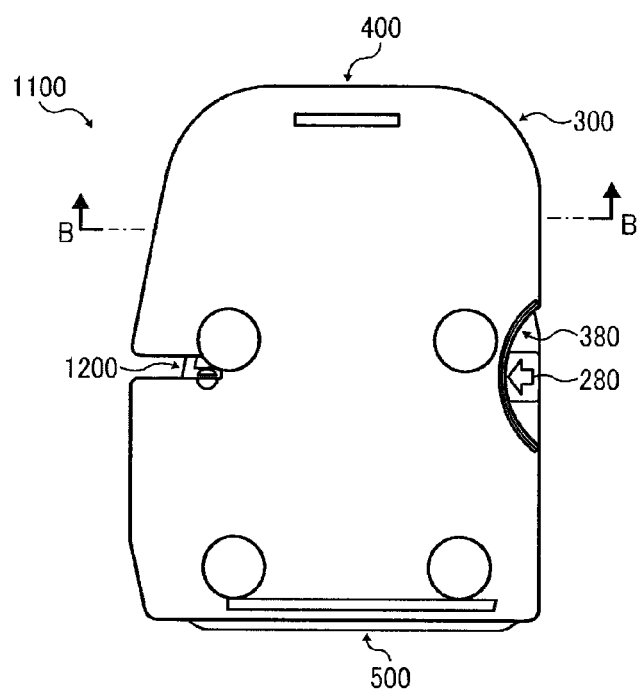

FIGS. 3A and 3B each show an assembling operation of the impact detector according to the first embodiment, in which FIG. 3A is a plan view showing a state in which the front case member covers the second rear case member, and FIG. 3B is a plan view showing a first combination position by the front case member and the second rear case member.

As illustrated in FIG. 3, the case 110 is assembled such that, first, the second rear case member 1200 and the front case member 300 are engaged, the front case member 300 is slid leftward relative to the second rear case member 1200, and the second rear case member 1200 and the front case member 300 are laterally moved so as to be assembled together. When assembled, an upper-side detention device 400 is created at an upper end where the second rear case member 1200 and the front case member 300 are closely contacted. Similarly, a lower-side detention device 500 is created at a bottom end where the second rear case member 1200 and the front case member 300 are closely contacted. As will be described later, the upper-side detention device 400 and the lower-side detection device 500 prevent the second rear case member 1200 and the front case member 300 from returning from the first combination position or from the assembled state and prevent the second rear case member 1200 from coming off from the front case member 300. The upper-side detention device 400 and the lower-side detection device 500 prevent the second rear case member 1200 and the front case member 300 from returning from a second combination position for shock sensing to the first combination position and prevent incapable state of the impact or the tilt. Herein, in the second combination position, the impact detector 100 is disposed on a package or the like and comes into an impact sensing state. The assembled structure is the same for the first impact detector 100 using the first rear case member 200.

In general, considering the fact that a user touches a central, left end portion of the front case member 300 when sliding the front case member 300 leftward, the impact detectors 100, 1100 according to the first embodiment include the upper-side detention device 400 and the lower-side detention device 500 disposed at the both upper and lower sides. With this structure, while preventing the tilt between the first rear case member 200 and the front case member 300 in the sliding movement, the front case member 300 can be moved smoothly.

Figure 4:
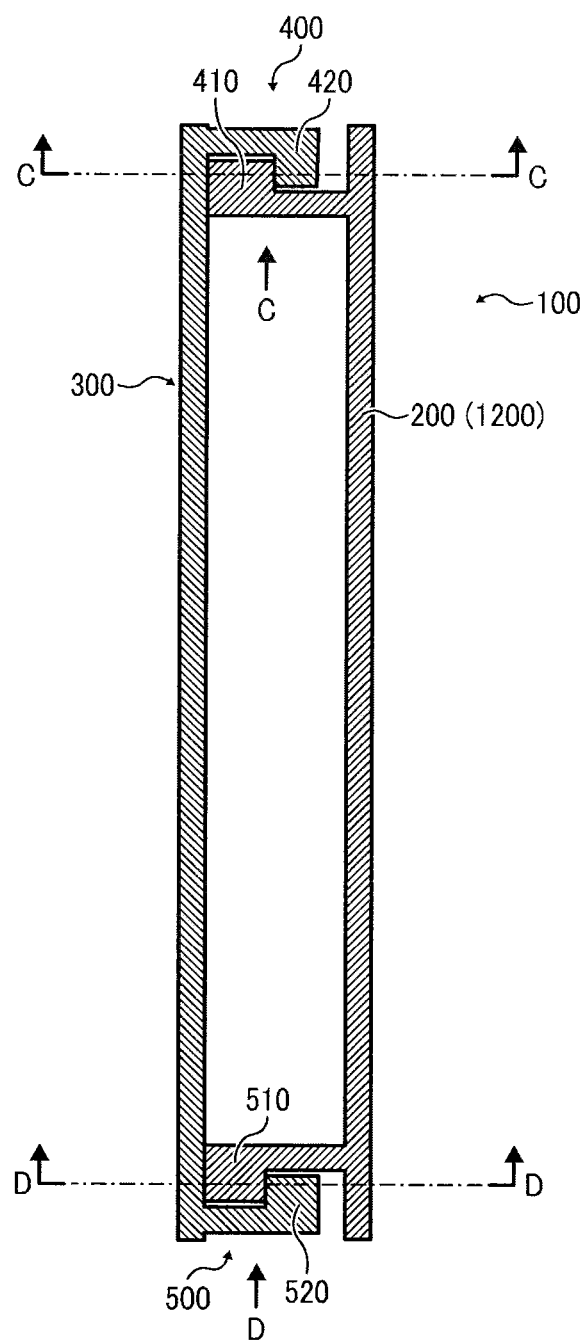
FIG. 4 is a schematic cross-sectional view illustrating an assembled state of the impact detector according to the first embodiment along Line A-A in FIG. 3A.

FIG. 4 is a schematic cross-sectional view illustrating an assembled state of the impact detector according to the first embodiment along Line A-A in FIG. 3. The upper-side detention device 400 is configured such that a rear-side detention step 410 formed on the first rear case member 200 is slid in and engaged with a front-side detention step 420 formed on the front case member 300. In addition, the lower-side detention device 500 is configured such that a rear-side detention step 510 formed on the first rear case member 200 is slid in and engaged with a front-side detention step 520 formed on the front case member 300.

With the first rear case member 200 covered by the front case member 300, the front case member 300 is slid leftward so that the upper-side detention device 400 and the lower-side detention device 500 come to the first combination position from a state in which the first rear case member 200 is not engaged with the front case member 300, and from the first combination position to the second combination position.

In the first combination position, the first rear case member 200 and the front case member 300 are ready for shipping, are in a state incapable of sensing the impact, and are prevented from disengaging from each other. In the second combination position, the impact detector 100 is attached to the packing and the like and is capable of sensing the impact.

A click is felt each time the upper-side detention device 400 and the lower-side detention device 500 moves on to the first combination position where the front case member 300 is shifted leftward over the first rear case member 200 from a state simply covering the first rear case member 200; and when moving to the second combination position. The upper-side detention device 400 and the lower-side detection device 500 prevent the first rear case member 200 and the front case member 300 from moving inversely. In addition, resistance of the upper-side detention device 400 when the first rear case member 200 and the front case member 300 moves from the first combination position to the second combination position is greater than when the first rear case member 200 and the front case member 300 moves to the first combination position from a state in which the front case member 300 simply covers the first rear case member 200.

First, the upper-side detention device 400 will be described.

Figure 5A:
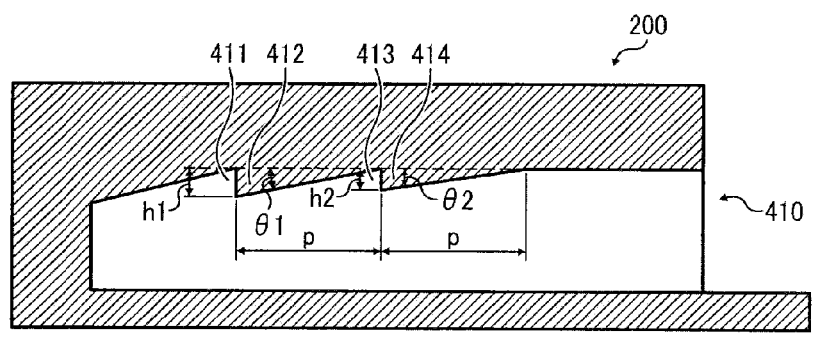
Figure 5B:
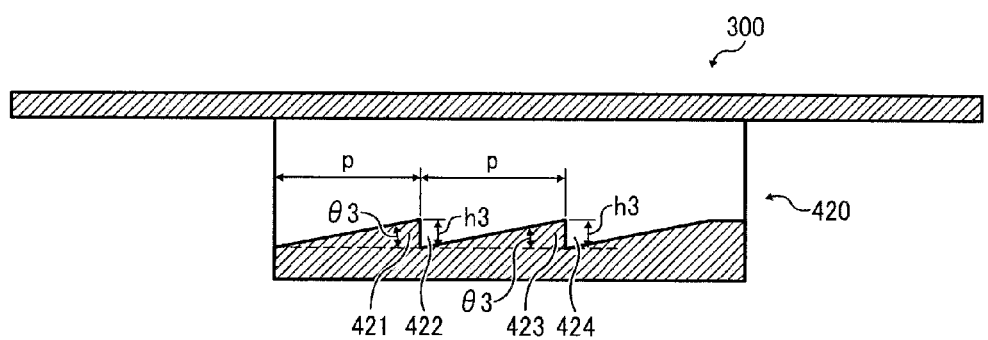

FIGS. 5A and 5B are an upper-side detention device of the impact detector according to the first embodiment along Line C-C in FIG. 4 seen from the arrow direction, of which FIG. 5A is an end view of the rear case member and FIG. 5B is an end view of the front case member. The upper-side detention device 400 includes the rear-side detention step 410 formed at the first rear case member 200 and the front-side detention step 420 formed at the front case member 300. The rear-side detention step 410 includes two recessed portions, that is, a first recess 411 and a second recess 413; and two peak portions, that is, a first peak 412 and a second peak 414. The recesses and the peaks are alternatingly formed with a same pitch 'p'. The first peak 412 and the second peak 414 each are a right-angled triangle with a peak and a slope downward. The peaks may include an arc shape. The impact detector 100 according to the present embodiment includes the first peak 412 having a height h1 higher than a height h2 of the second peak 414 (h1>h2). In addition, a tilt angle θ1 of the first peak 412 is greater than a tilt angle θ2 of the second peak 414 (θ1>θ2). In this example, θ1 is set to 24 degrees and θ2 is set to 20 degrees.

The front-side detention step 420 includes two peak portions, that is, a first peak 421 and a second peak 423; and two recessed portions, that is, a first recess 422 and a second recess 424. The recesses and the peaks are alternately formed with the same pitch 'p' as that of the rear-side detention step 410. The first peak 421 and the second peak 423 each are a right-angled triangle with an upward peak and an upward slope contrary to the rear-side detention step 410. Peaks are arc-shaped. In the present impact detector 100, the first peak 421 and the second peak 423 have a same height h3 and the first peak 421 and the second peak 423 have a same tilt angle θ3. In this example, θ3 is set to 24 degrees.

Figure 6A:
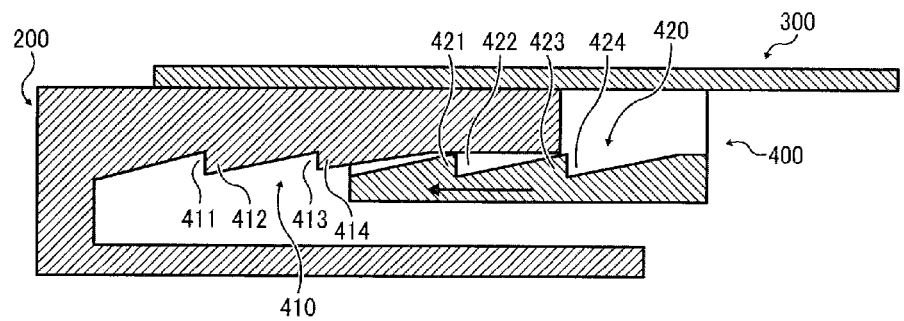
Figure 6B:
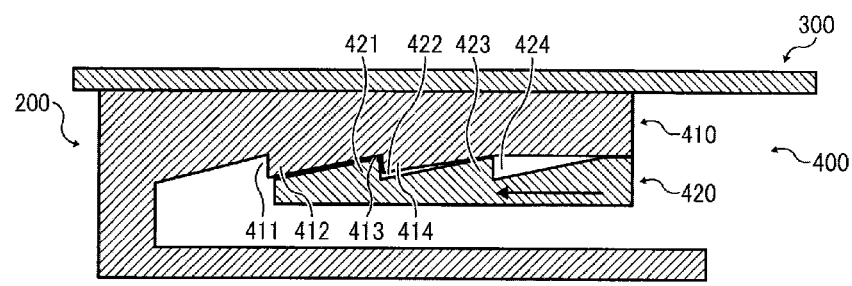
Figure 6C:
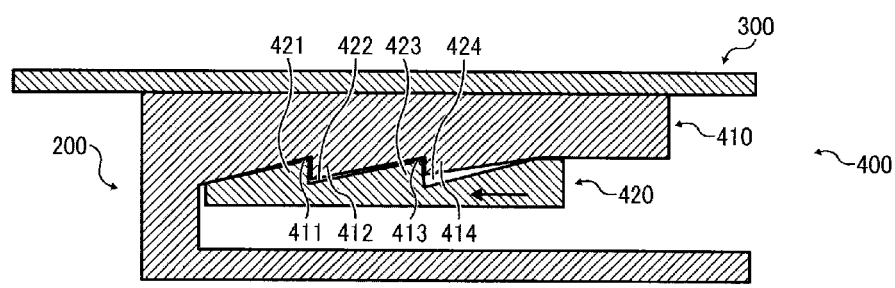

When the front case member 300 covers the first rear case member 200 and the front case member 300 slides leftward, the present upper-side detention device 400 function as illustrated in FIGS. 6A-6C. FIGS. 6A to 6C show operations of the upper-side detention device 400 as illustrated in FIGS. 5A and 5B, of which FIG. 6A is an end view showing a state in which the front case member covers the first rear case member; FIG. 6B is an end view showing the first combination position; and FIG. 6C is an end view showing the second combination position. Specifically, in the first combination position (see FIG. 6B) from the state in which the front case member 300 covers the first rear case member 200 and the front case member 300 is slid slightly (see FIG. 6A), the first peak 421 of the front-side detention step 420 crosses the second peak 414 of the rear-side detention step 410 and comes in the second recess 413 of the rear-side detention step 410 (see FIG. 6B). Similarly, the second peak 414 of the rear-side detention step 410 crosses the first peak 421 of the front-side detention step 420 and comes in the first recess 422 of the front-side detention step 420. Then, the first peak 421 of the front-side detention step 420 and the second peak 414 of the rear-side detention step 410 engage each other, so that moving in an opposite direction (rightward move) by the first rear case member 200 and the front case member 300 is prevented. In addition, when each peak crosses the other peak, the member forming the upper-side detention device 400 is deformed elastically and returns to an original shape after the completion of crossing over.

In addition, in the move to the first combination position, each time the second peak 414 of the rear-side detention step 410 crosses over the second peak 423 of the front-side detention step 420 to enter the first recess 422 and similarly, each time the first peak 421 of the front-side detention step 420 crosses over the second peak 414 of the rear-side detention step 410 to enter the second recess 413 of the rear-side detention step 410, a click is felt as well as a resistive force.

Accordingly, the first rear case member 200 and the front case member 300 are held in the assembled state being the first combination position in which the impact detector can be shipped. In the lateral direction sensor section 180, moving of the first weight 120 is prevented by stoppers 391, 392 (see FIG. 9A) disposed in the right-side weight path 140 and the left-side weight path 150.

Further, when the first rear case member 200 and the front case member 300 comes to the second combination position from the first combination position, the upper-side detention device 400 functions in the following manner (see FIGS. 6B and 6C). Specifically, the first peak 421 and the second peak 423 of the front-side detention step 420 cross over the first peak 412 and the second peak 414 of the rear-side detention step 410 and enter the first recess 411 and the second recess 413 of the rear-side detention step 410, respectively. Similarly, the first peak 412 and the second peak 414 of the rear-side detention step 410 cross over the first peak 421 and the second peak 423 of the front-side detention step 420 and enter the first recess 422 and the second recess 424 of the front-side detention step 420, respectively. When each peak crosses over the other peak, a member forming the upper-side detention device 400 is deformed elastically and returns to an original shape after the completion of crossing over.

Then, the first peak 421 and the second peak 423 of the front-side detention step 420 and the first peak 412 and the second peak 414 of the rear-side detention step 410 engage each other, so that moving in an opposite direction (rightward move) by the first rear case member 200 and the front case member 300 is prevented.

In the moving to the second combination position, two peaks 412, 414 of the rear-side detention step 410 cross over the two peaks 421, 423 of the front-side detention step 420 and enter the two recesses 422, 424. Similarly, the first peak 421 and the second peak 423 of the front-side detention step 420 cross over the first peak 412 and the second peak 414 of the rear-side detention step 410 and enter the first recess 411 and the second recess 413 of the rear-side detention step 410, respectively. This time, the 'click' feeling is given as well as the resistive force. Because the height h1 of the first peak 412 of the rear-side detention step 410 that the first peak 421 of the front-side detention step 420 has to cross over is higher than the height h2 of the second peak 414, the resistive force increases.

Next, the lower-side detention device 500 will be described.

FIGS. 7A and 7B show states of the lower-side detention device of the impact detector according to the first embodiment along Line D-D in FIG. 4, of which FIG. 7A is an end view of the rear case member and FIG. 7B is an end view of the front case member. The lower-side detention device 500 includes a structure substantially identical to that of the upper-side detention device 400.

The lower-side detention device 500 includes the rear-side detention step 510 formed at the first rear case member 200 and the front-side detention step 520 formed at the front case member 300. The rear-side detention step 510 includes two recessed portions, that is, a first recess 511 and a second recess 513; and two peak portions, that is, a first peak 512 and a second peak 514. The recesses and the peaks are alternately formed with a same pitch 'p'. The first peak 512 and the second peak 514 each are a right-angled triangle with a downward peak and a downward slope. Peaks are arc-shaped. The impact detector 100 according to the present embodiment includes the first peak 512 having a height h4 higher than a height h5 of the second peak 514 (h4>h5). In addition, a tilt angle θ4 of the first peak 512 is greater than a tilt angle θ5 of the second peak 514 (θ4>θ5). In this example, θ4 is set to 24 degrees and θ5 is set to 20 degrees.

In addition, the front-side detention step 520 includes two peak portions, that is, a first peak 521 and a second peak 523;

and two recessed portions, that is, a first recess 522 and a second recess 524. The recesses and the peaks are alternately formed with the same pitch 'p' as that of the rear-side detention step 510. The first peak 521 and the second peak 523 each are a right-angled triangle with an upward peak and an upward slope contrary to the rear-side detention step 510. Peaks are arc-shaped. In the present impact detector 100, the first peak 521 and the second peak 523 have a same height h6 and the first peak 521 and the second peak 523 have a same tilt angle θ6. In the present example, θ6 is set to 24 degrees.

Figure 8A:
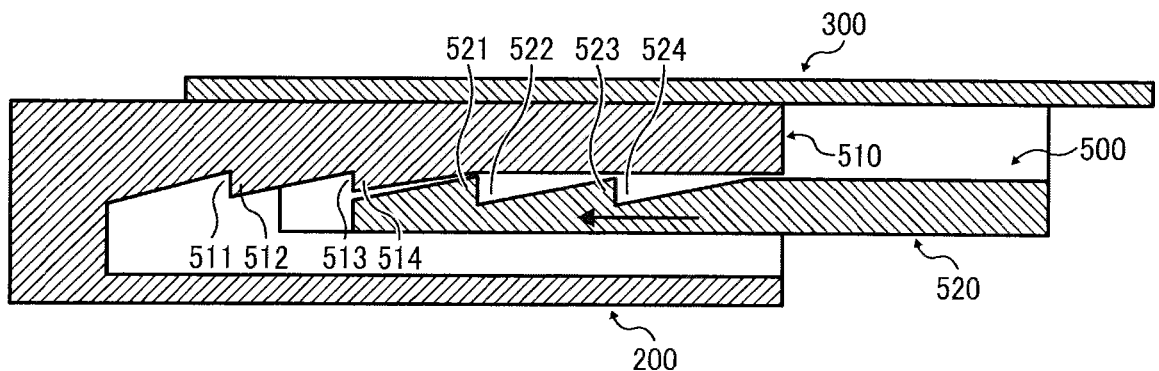
Figure 8B:
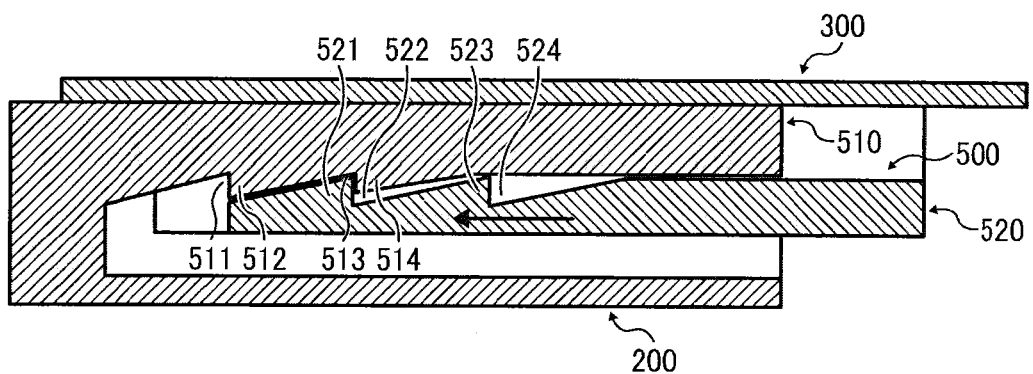
Figure 8C:
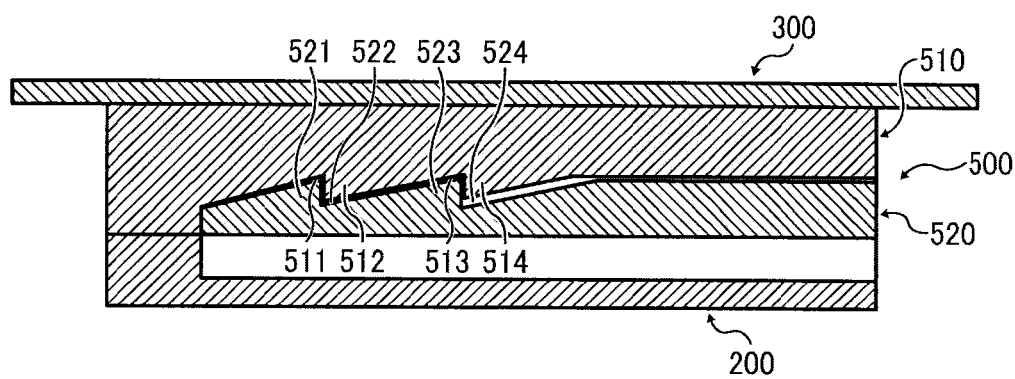

When the front case member 300 covers the first rear case member 200 and the front case member 300 slides leftward, the present lower-side detention device 500 functions in the following manner. FIGS. 8A to 8C show operations of the lower-side detention device 500 as illustrated in FIGS. 7A and 7B, of which FIG. 8A is an end view showing a state in which the front case member covers the first rear case member; FIG. 8B is an end view showing the first combination position thereof; and FIG. 8C is an end view showing the second combination position thereof. Specifically, in the first combination position (see FIG. 8B) from the state in which the front case member 300 just covers the first rear case member 200 (see FIG. 8A), the first peak 521 of the front-side detention step 520 crosses over the second peak 514 of the rear-side detention step 510 and comes in the second recess 513 of the rear-side detention step 510. Similarly, the second peak 514 of the rear-side detention step 510 crosses over the first peak 521 of the front-side detention step 520 and comes in the first recess 522 of the front-side detention step 520. Then, the first peak 521 of the front-side detention step 520 and the second peak 514 of the rear-side detention step 510 engage each other, so that moving in an opposite direction (rightward move) by the front case member 300 relative to the first rear case member 200 is prevented. When each peak crosses over the other peak, a member forming the upper-side detention device 400 is deformed elastically and returns to an original shape after the completion of crossing over.

In addition, in the move to the first combination position, each time the second peak 514 of the rear-side detention step 510 crosses over the second peak 523 of the front-side detention step 520 to enter the first recess 522, and similarly, each time the first peak 521 of the front-side detention step 520 crosses over the second peak 514 of the rear-side detention step 510 to enter the second recess 513 of the rear-side detention step 510, a click is felt as well as a resistive force.

Accordingly, the first rear case member 200 and the front case member 300 are held in the assembled state being the first combination position in which the impact detector can be shipped. When each peak crosses over the other peak, the member forming the upper-side detention device 400 is deformed elastically and returns to an original shape after the completion of crossing over.

Further, when the first rear case member 200 and the front case member 300 come into the second combination position from the first combination position, the lower-side detention device 500 functions in the following manner (see FIG. 8C). Specifically, the first peak 521 and the second peak 523 of the front-side detention step 520 cross over the first peak 512 and the second peak 514 of the rear-side detention step 510 and come into the first recess 511 and the second recess 513 of the rear-side detention step 510, respectively.

Similarly, the first peak 512 and the second peak 514 of the rear-side detention step 510 cross over the first peak 521 and the second peak 523 of the front-side detention step 520 and enter the first recess 522 and the second recess 524 of the front-side detention step 520, respectively. Then, the first peak 521 and the second peak 523 of the front-side detention step 520 and the first peak 512 and the second peak 514 of the rear-side detention step 510 engage each other, so that moving in an opposite direction (rightward move) by the front case member 300 relative to the first rear case member 200 is prevented.

In the moving to the second combination position, two peaks 512, 514 of the rear-side detention step 510 cross over the two peaks 521, 523 of the front-side detention step 520 and enter the two recesses 522, 524. Similarly, the first peak 521 and the second peak 523 of the front-side detention step 520 cross over the first peak 512 and the second peak 514 of the rear-side detention step 510 and enter the first recess 511 and the second recess 513 of the rear-side detention step 510, respectively. At this time, the click as well as the resistive force are felt. In this case, because the height h4 of the first peak 521 of the rear-side detention step 520 that the first peak 521 of the front-side detention step 520 has to cross over is higher than the height h5 of the second peak 514, the resistive force increases.

As described above, the resistive force when the first rear case member 200 and the front case member 300 move from the first combination position to the second combination position is greater than that when the first rear case member 200 and the front case member 300 move from the state in which the first rear case member 200 and the front case member 300 are simply engaged, to the first combination position. As a result, it is prevented to erroneously set the impact detector 100 to the second combination position in the assembly of the impact detector 100. This structural concept is applied to a case of assembling the second impact detector 1100 that employs the second rear case member 1200.

The upper-side detention device 400 and the lower-side detection device 500 simultaneously function when slidably moving the front case member 300 relative to the first rear case member 200. To make the relative movement of the first rear case member 200 and the front case member 300 smoother, the upper-side detention device 400 and the lower-side detention device 500 are preferably disposed at the same position in the width direction of the first rear case member 200 and the front case member 300.

In addition, shapes and numbers of the peaks and the recesses of the upper-side detention device 400 and the lower-side detention device 500 may be appropriately selected without being limited to the examples described herein. Further, although the present embodiment discloses a structure in which the angles of the peaks are formed differently; however, the angles thereof may be identically formed and instead, a surface of the recess opposite the peak may be coated with a low-friction member or may be subjected to low-friction processing only in the second combination position. Further, the structure is not limited to one using the peaks and recesses in combination, and another structure such as a non-return structure formed of pins and elastic members may also be used.

Further, the impact detector 100 or 1100 is configured such that the first rear case member 200 or the second rear case member 1200 combined with the front case member 300 are movable from an engaging state at a start of assembly to the first combination position (with a resistive force F1) after the completion of the assembly, and further movable from the first combination position to the second combination position (with a resistive force F2). The resistive forces F1 and F2 sequentially increase. In addition, the present embodiment includes a third combination position (with a resistive force F3), in which the detected shock is stored. Furthermore, the present embodiment includes a fourth position (with a resistive force F4), in which the impact detector is disassembled.

The resistive force F3 in which the detected shock is stored is between F1 and F2, and the resistive force F4 in the disassembled state is preferably the same as that of F3.

Further, in the impact detectors 100, 1100 according to the first embodiment, the first rear case member 200 and the front case member 300 are relatively movable as a whole. However, a part of either the first rear case member 200 or the second rear case member 1200 and the front case member 300 may be formed as a movable part which can be replaced with another part, so that the movable part can be moved to the other part in the assembly process. Between the movable part and the other part, the detention device as described above may be disposed.

Figure 9A:
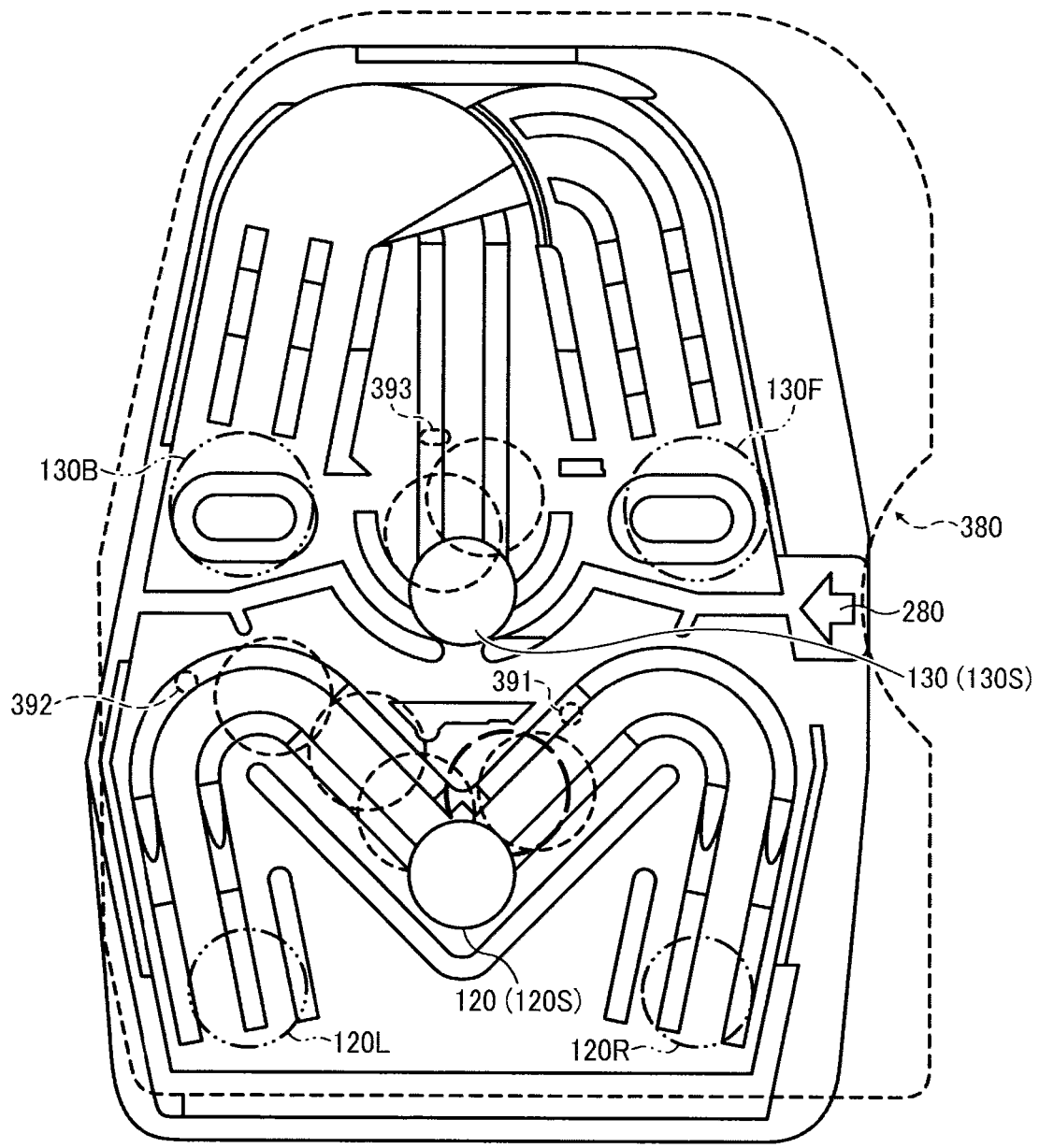
Figure 9B:
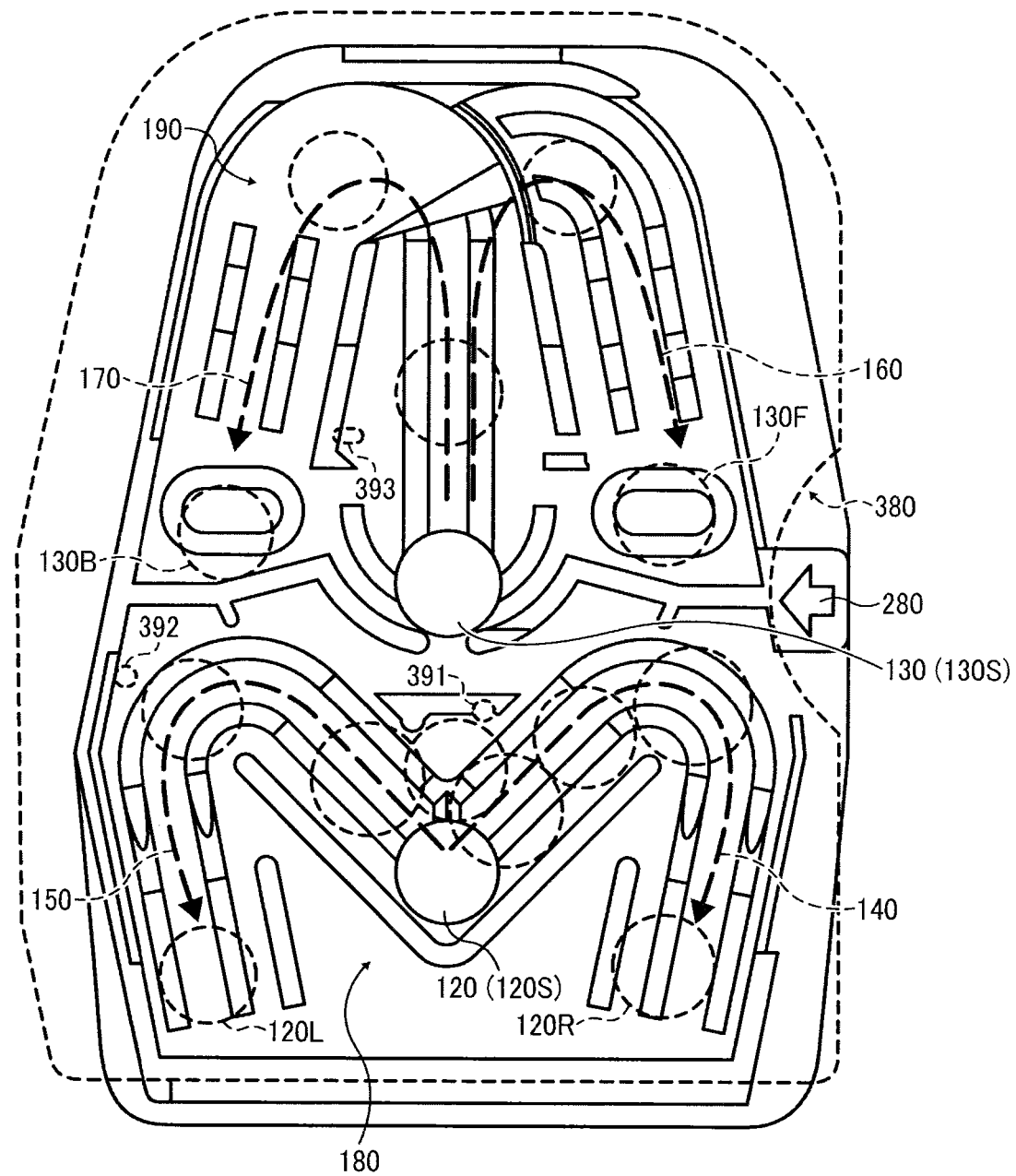

The impact detectors 100, 1100 according to the first embodiment further includes a switching means which prevents the first weight 120 and the second weight 130 from moving from the initial position 120S and the initial position 130S, respectively, in the first combination position. FIGS. 9A to 9B each show a moving range of the weight of the impact detector according to the first embodiment, in which FIG. 9A is a plan view showing the first combination position and FIG. 9B is a plan view showing the second combination position. The examples in FIGS. 9A and 9B employ the first rear case member 200; however, even though the second rear case member 1200 is used, the switching means exerts the same function.

The impact detector 100 employs, as switching means, stoppers 391, 392, and 393 disposed on the front case member 300. As illustrated in FIG. 9A, in a shipping state, that is, when the first rear case member 200 and the front case member 300 are positioned in the first combination position, the stoppers 391, 392 formed on the front case member 300 are positioned in the right-side weight path 140 and the left-side weight path 150, and the stopper 393 is positioned in the proximal weight path 160 and the distal weight path 170. As a result, the first weight 120 does not move from the initial position 120S to the right-side detection position 120R or the left-side detection position 120L. In addition, the second weight 130 does not move from the initial position 130S to the proximal detection position 130F or the distal detection position 130B.

As illustrated in FIG. 9B, in an impact detecting state, that is, when the first rear case member 200 and the front case member 300 are positioned in the second combination position, the stoppers 391, 392, and 393 are away from each of the right-side weight path 140, the left-side weight path 150, the proximal weight path 160, and the distal weight path 170. As a result, the impact detector 100 is brought into a state detecting the impact or force due to the turnover in the front-back direction or in the lateral direction.

Figure 10A:
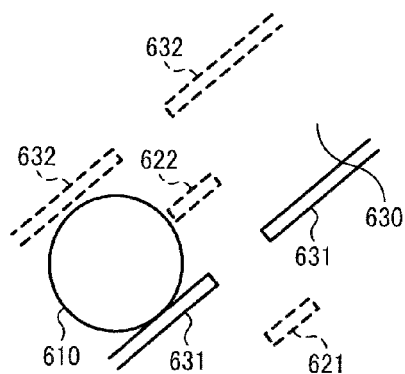
FIGS. 10A and 10B are schematic views showing other switching means.
Figure 10B:
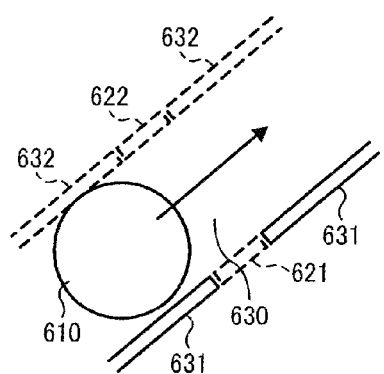

However, the switching means is not limited to the aforementioned structure. FIGS. 10 to 12 are schematic views illustrating examples of other switching means. The structure to move the switching means to the first combination position or the second combination position is the same as described above, and therefore, detailed description thereof is omitted. FIGS. 10A and 10B show a case in which a part of the front case member 300 is formed as a movable portion, not shown, of a weight 610 relative to the rest of the front case member 300, and regulating members 621, 622 to prevent the move of the weight 610 are formed at the movable portion. In the present example, the regulating members 621, 622 become a part of protruded members 631, 632 built to form a weight path 630 as illustrated in FIG. 10B. Then, in the first combination position as illustrated in FIG. 10A, the regulating members 621, 622 are so positioned as to narrow the weight path 630. In such a state, moving of the weight 610 is prevented. In this example, the protruded member 631 represented by a solid line is disposed at the first rear case member 200 and the protruded member 632 represented by a broken line and the regulating members 621, 622 are formed at the front case member 300.

Then, the moving part is slid to turn into the second combination position, and the regulating members 621, 622 are moved to be integrated with the protruded portions 631, 632 as illustrated in FIG. 9B. In this state, the weight 610 can move in the weight path 630.

In this example, the movable portion is formed on the front case member 300, thereby creating a regulating part. However, by forming a part of the front case member 300 as the movable portion, the regulating part can be disposed on the first rear case member 200. Further, the regulating parts are disposed at both sides of the weight path 630. However, by disposing the regulating part at one of the regulating members 621, 622, the weight path 630 may be formed with only one regulating part.

Figure 11A:
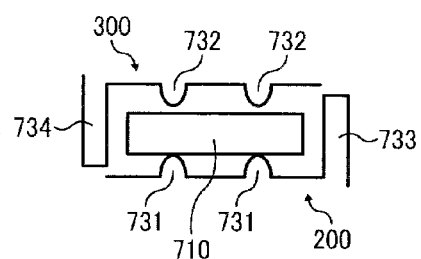
FIGS. 11A to 11C are schematic views showing other switching means.
Figure 11B:
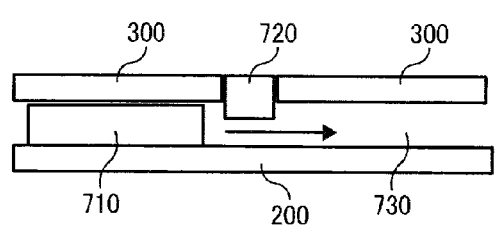
Figure 11C:
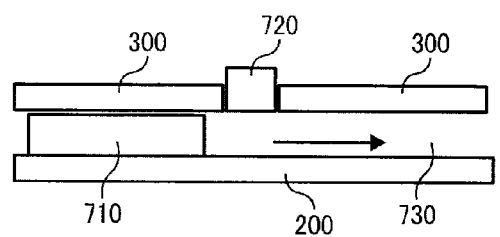
Figure 12:
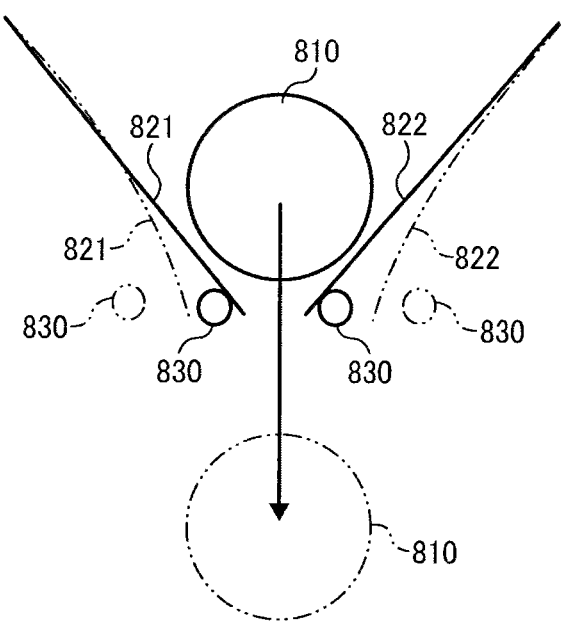
FIG. 12 is a schematic view showing another switching means.

FIGS. 11A to 11C show a case in which a part of the front case member 300 is formed as a movable portion, not shown, of a weight 710 relative to the rest of the front case member 300, and a regulating member 720 to prevent the move of the weight 710 is formed at the movable portion. At the first combination position as illustrated in FIG. 11B, the regulating member 720 is disposed at a position narrowing a weight path 730, so that the move of the weight 710 is prevented.

Then, the movable portion formed on the front case member 300 is moved to turn into the second combination position, and a regulating part 720 is moved, via a not-shown link, to a position as illustrated in FIG. 11C. In this state, the weight 730 can move in the weight path 730. The first rear case member 200 and the front case member 300 define the weight path 730, and each of the first rear case member 200 and the front case member 300 includes a rail 731 and a rail 732, respectively. In addition, the weight path 730 is formed between protruded members 733 and 734 built on the first rear case member 200 and the front case member 300, respectively.

In this example, the regulating part 720 is formed on the front case member 300; however, alternatively, the regulating part may be formed on the first rear case member 200 and a part of the front case member 300 may be defined as the movable portion. Further, the rails 731, 732 disposed on the first rear case member 200 and the front case member 300 are configured to move integrally.

Furthermore, an example as illustrated in FIG. 12 is applied to a case including a sensor 800 to detect an impact due to a fall by detecting the fall of a weight 810. In the sensor 800, the weight 810 is held between blade springs 821, 822, of which leading ends approach each other downwardly. Due to the impact of the fall, the weight 810 expands the blade springs 821, 822 as illustrated by a broken line in FIG. 12, and the thus-fallen weight 810 detects the impact. In this example, as a switching means, a part of the front case member 300 defined as a movable portion is slidably moved, so that pins 830 are laterally moved. When the movable portion is set to the first combination position, the pins 830 are positioned at the solid line positions, and, even when the weight is given a force from the impact, the blade spring 821 is prevented from deforming. As a result, the weight 810 does not fall.

Then, when the movable portion is set to the second combination position, the pins 830 move to a direction separating from the blade springs 821, 822 and the weight 810 falls due to the impact of the fall.

In addition, as the regulating member, various structures other than the ones described above may be used if appropriate.

As described heretofore, when the first impact detector 100 and the second impact detector 1100 are assembled and shipped as a commercial product, the front case member 300 is slid leftward from the state in which the front case member 300 covers the first rear case member 200 or the second rear case member 1200, and the front case member 300 with the first rear case member 200 or with the second rear case member 1200 are positioned to the first combination position. In the shipped state, the impact detector 100 does not sense the impact yet. The impact detector 100 or 1100 is attached to a vertical wall of the package and the front case member 300 is slid leftward, so that the first rear case member 200 or the second rear case member 1200 and the front case member 300 is set to the second combination position for sensing the impact.

The top plate 310 of the front case member 300 includes an arc-shaped pressing portion 380, which the finger is hung on to slide the front case member 300 leftward in the figure. In addition, a bottom plate 210 of the first rear case member 200 and the second rear case member 1200 includes an arrow-shape hole 280 observable from the arc-shaped pressing portion 380 when the first rear case member 200 or the second rear case member 1200 and the front case member 300 are set to the second combination position. As a result, it is securely observed that the case 110 is set to the second combination position in which the impact can be detected.

Next, details of the first rear case member 200, the second rear case member 1200, and the front case member 300 will be described.

Figure 13A:
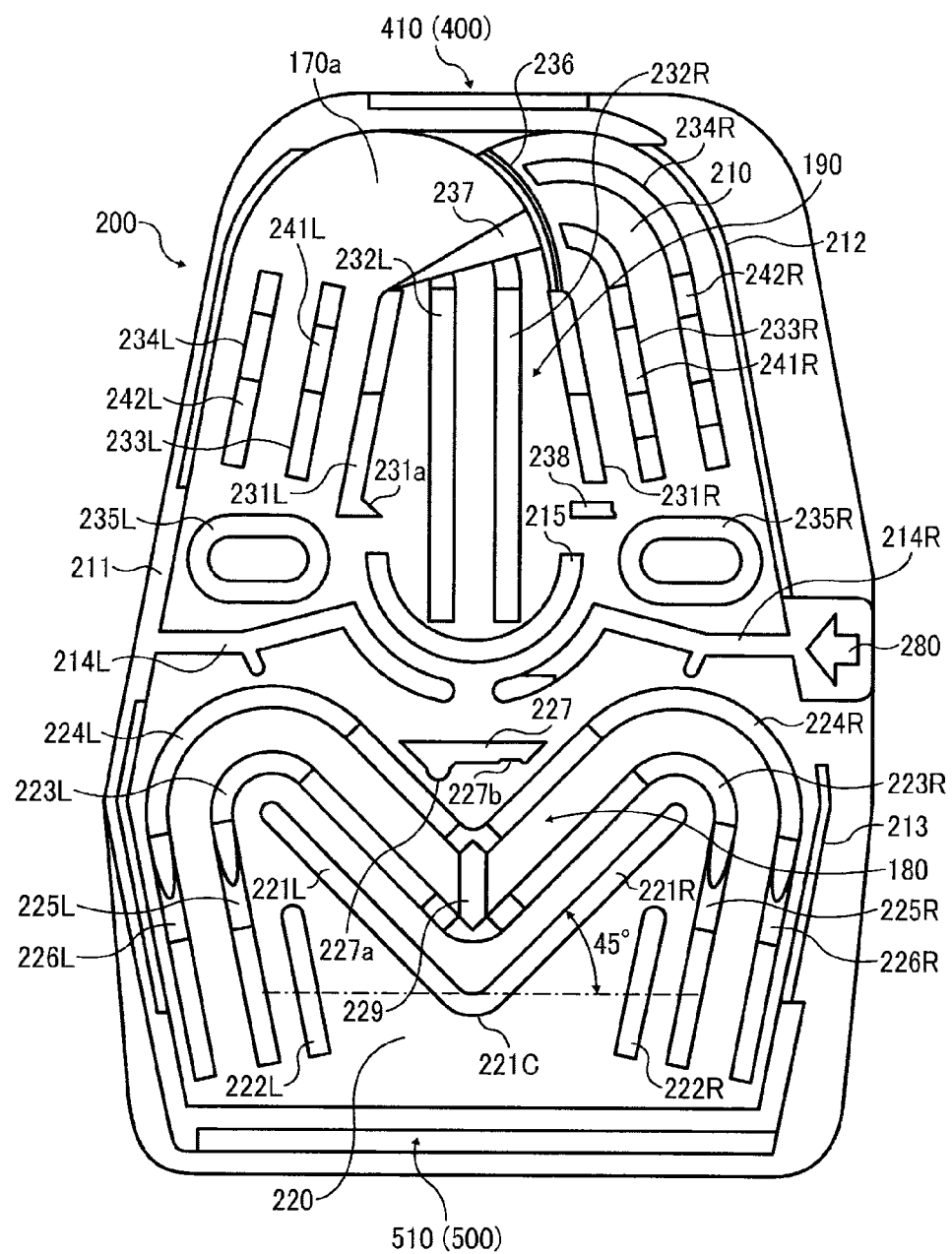
Figure 13B:
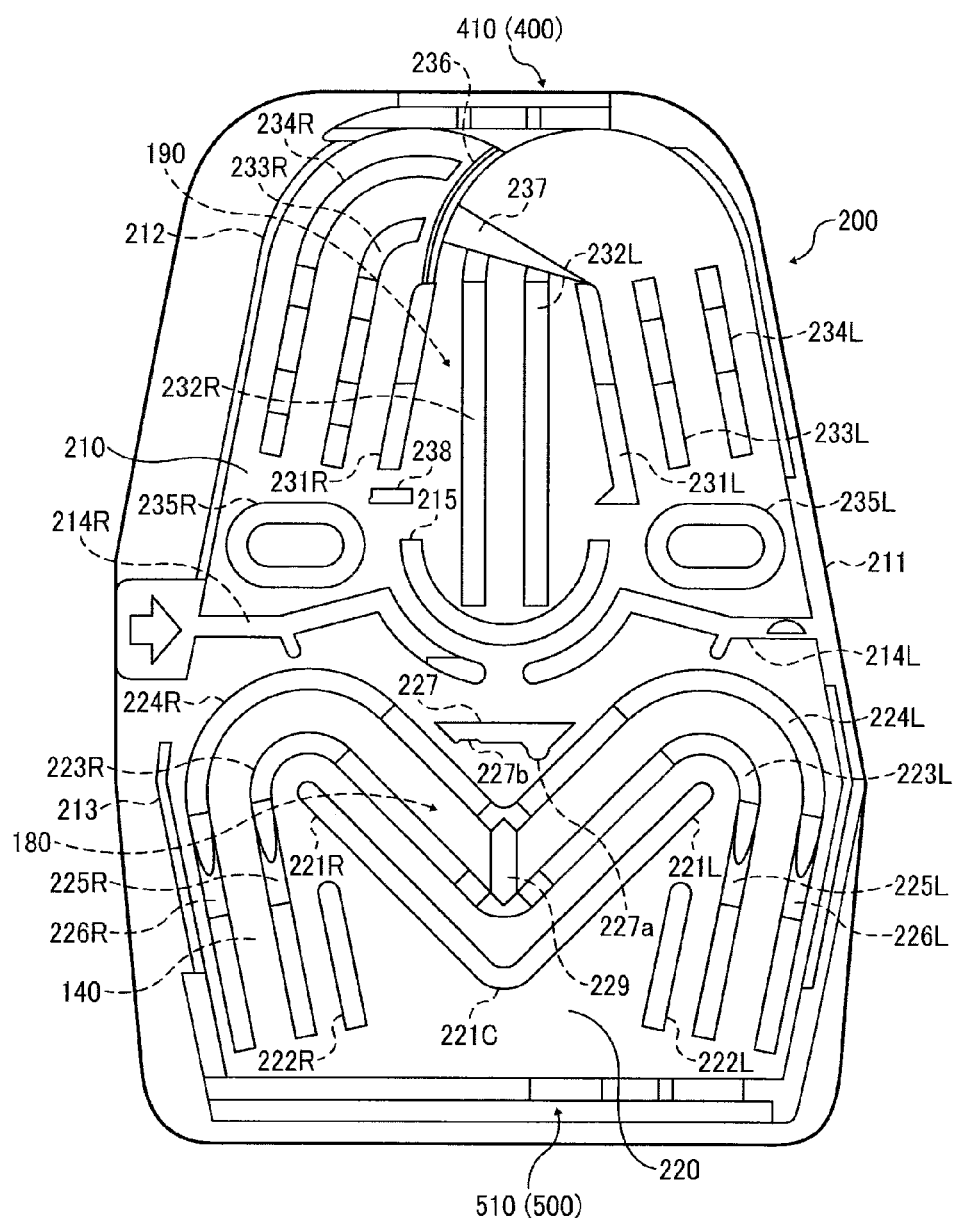
Figure 14A:
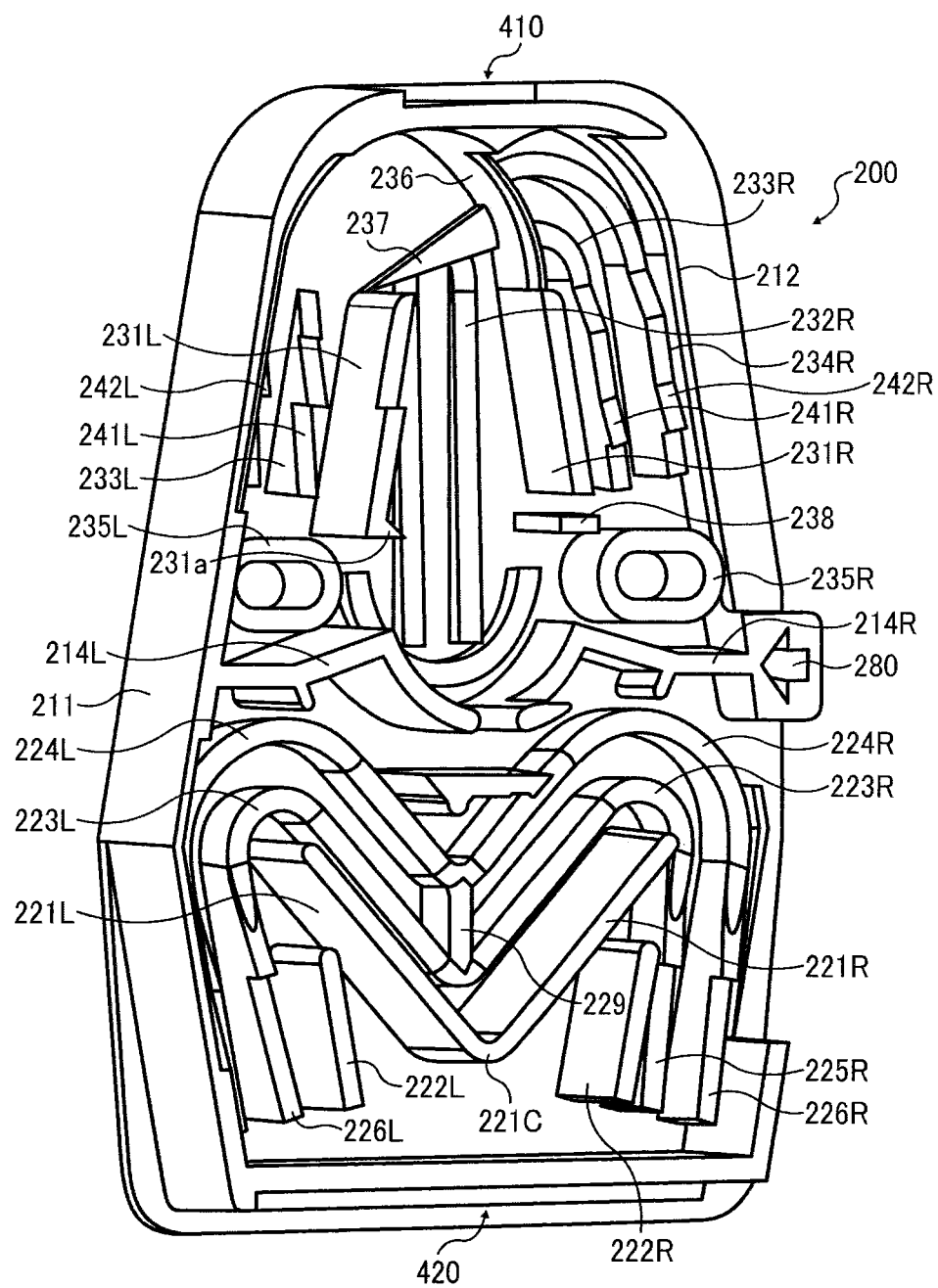
Figure 14B:
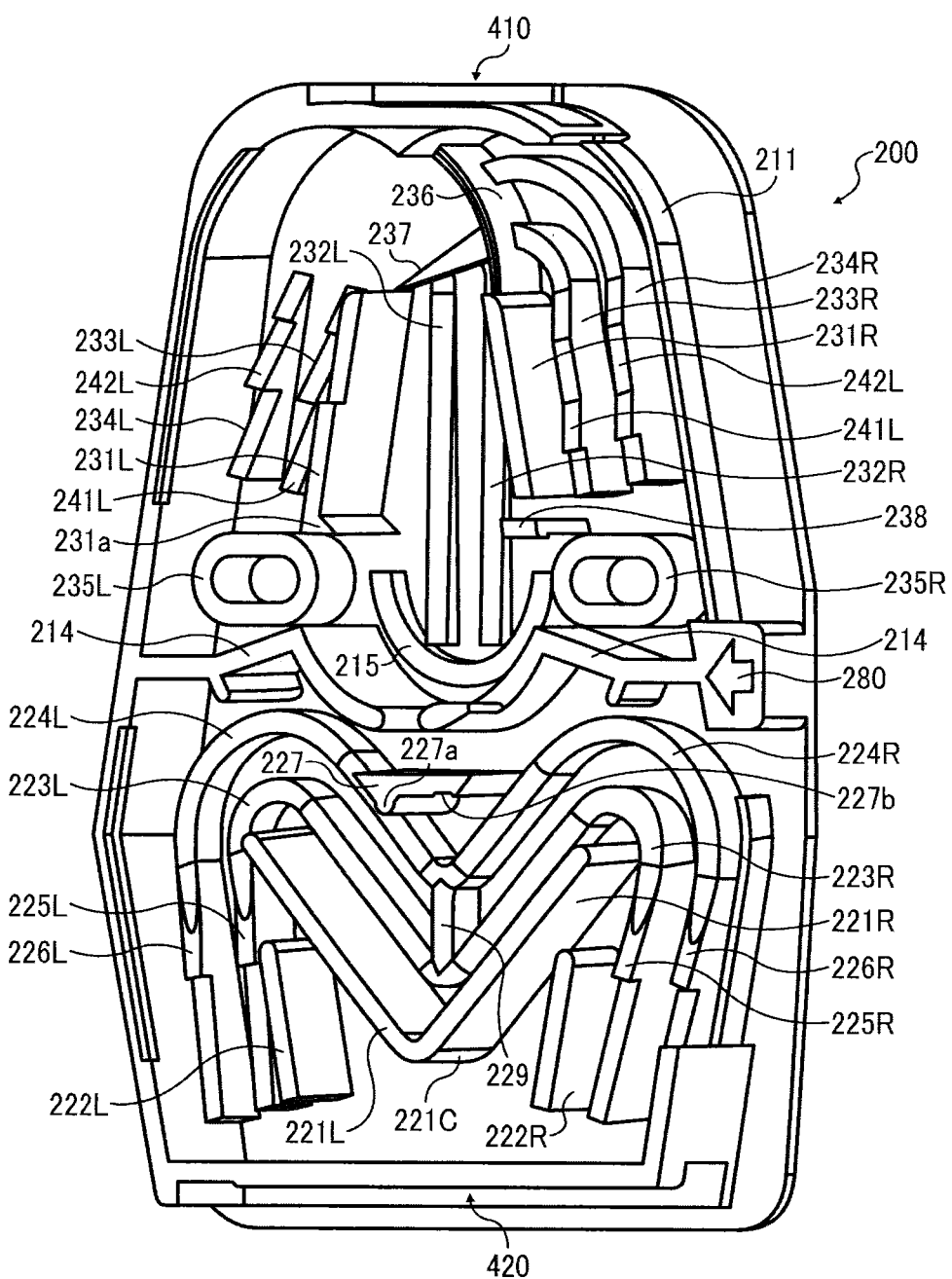
Figure 15A:
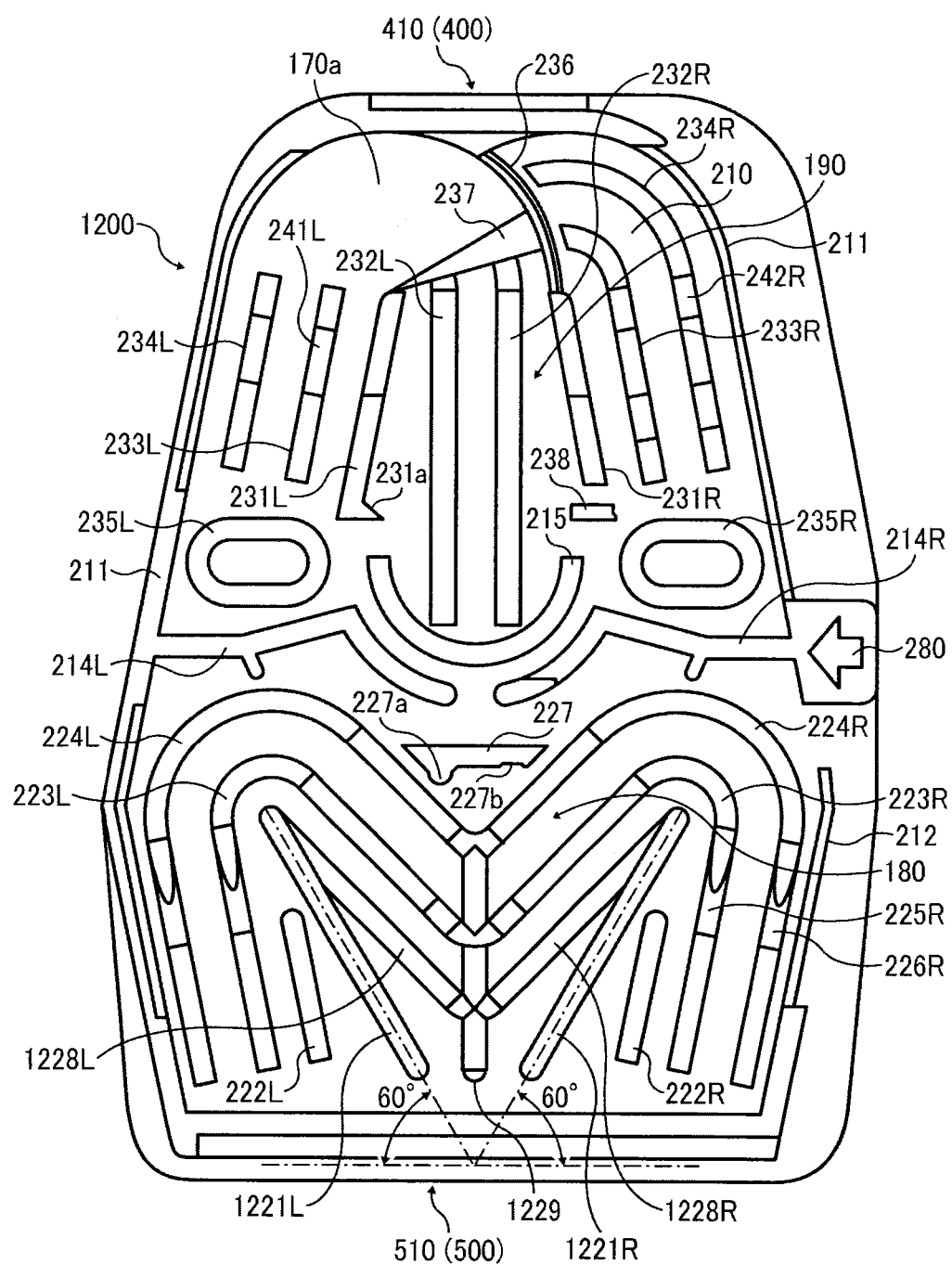
Figure 15B:
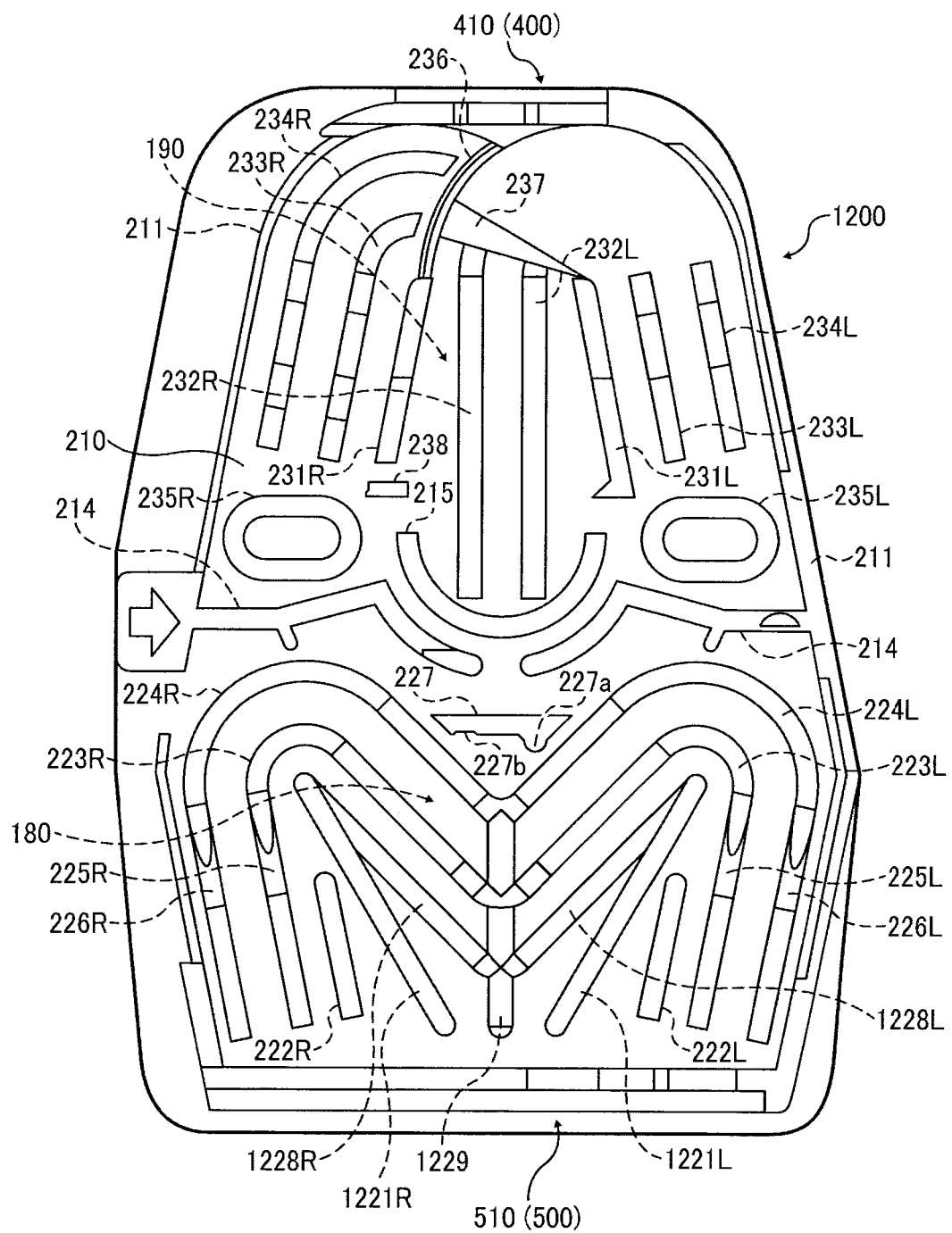
Figure 16A:
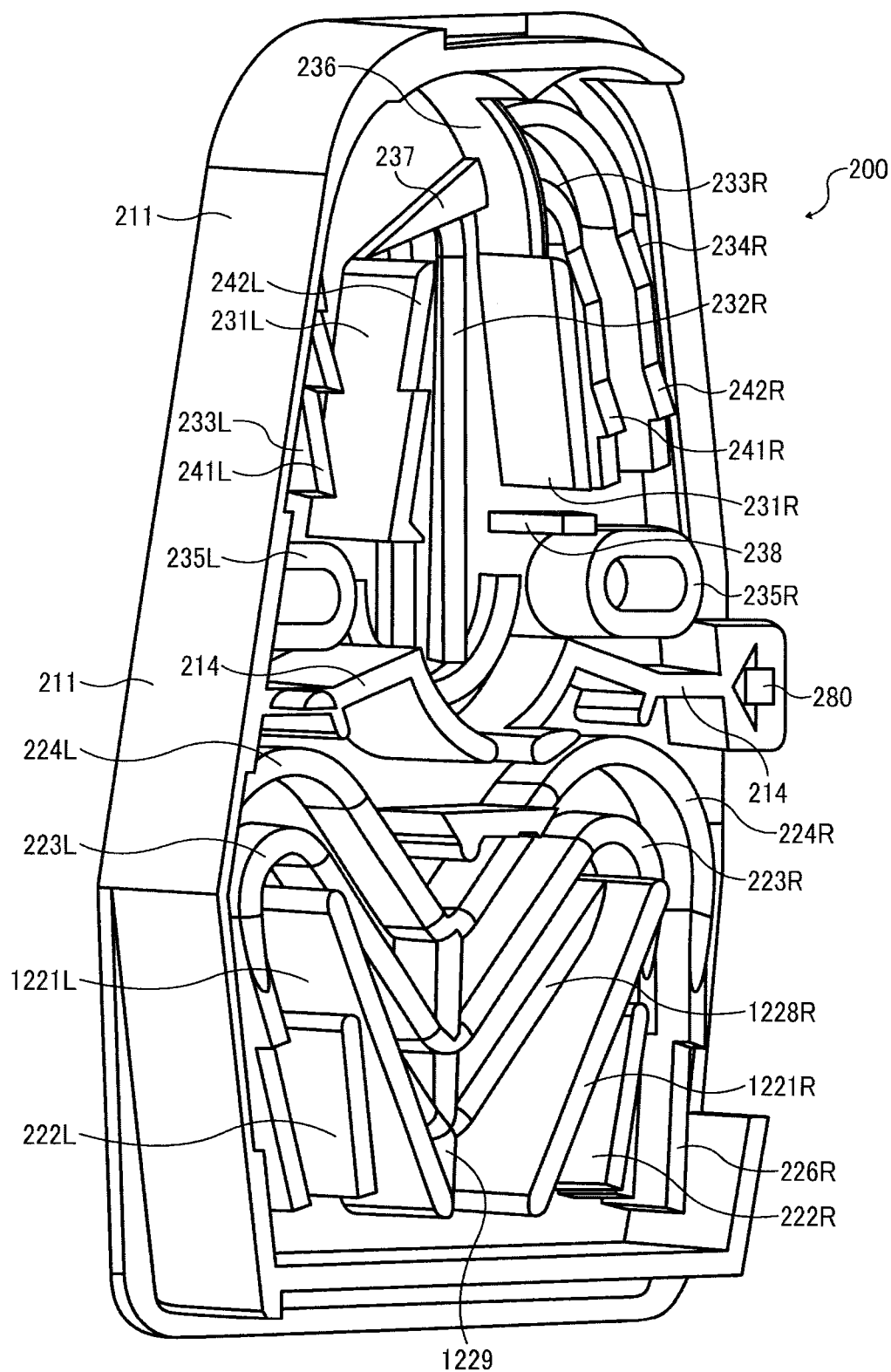
Figure 16B:
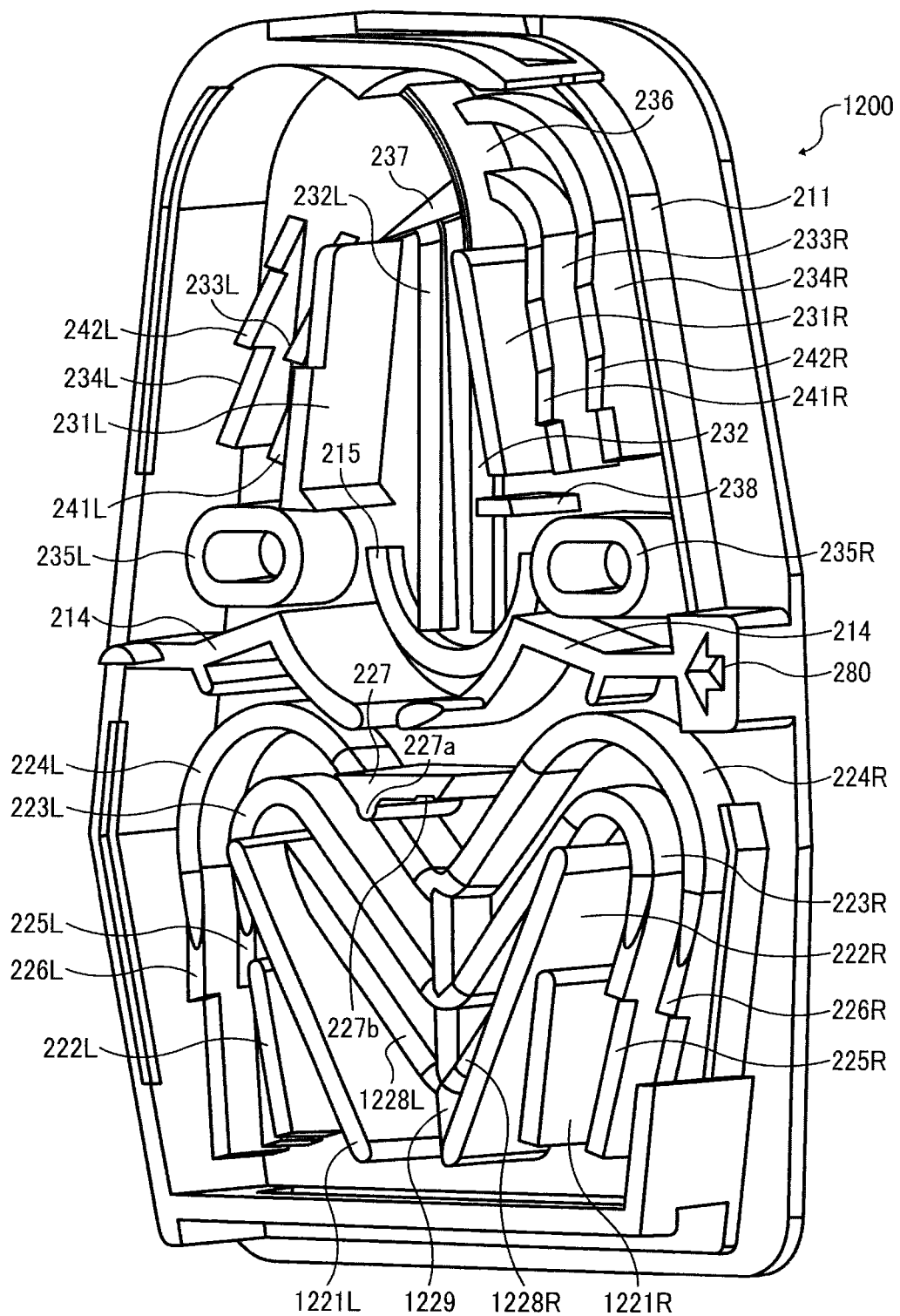
Figure 17A:
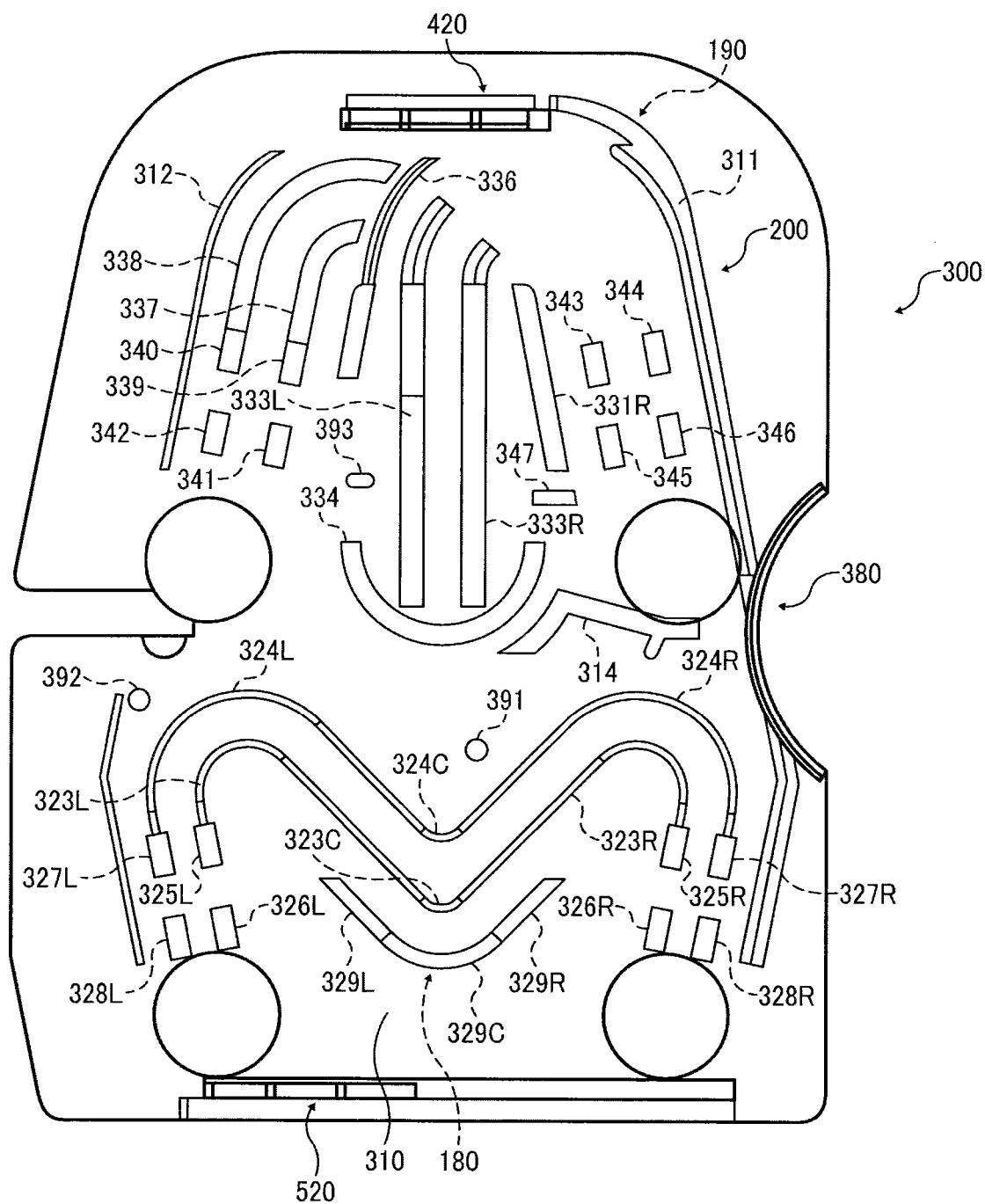
Figure 17B:
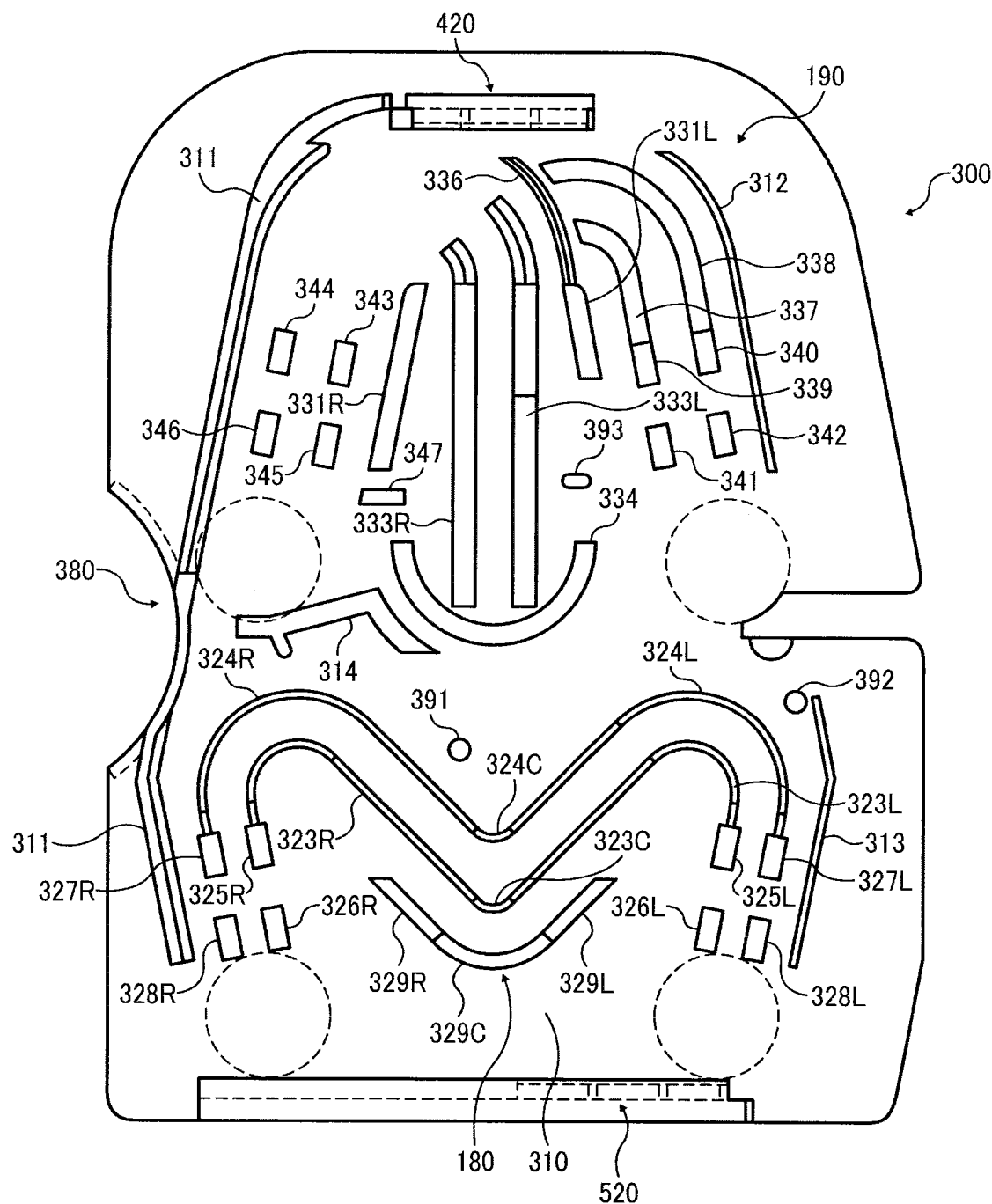
Figure 18A:
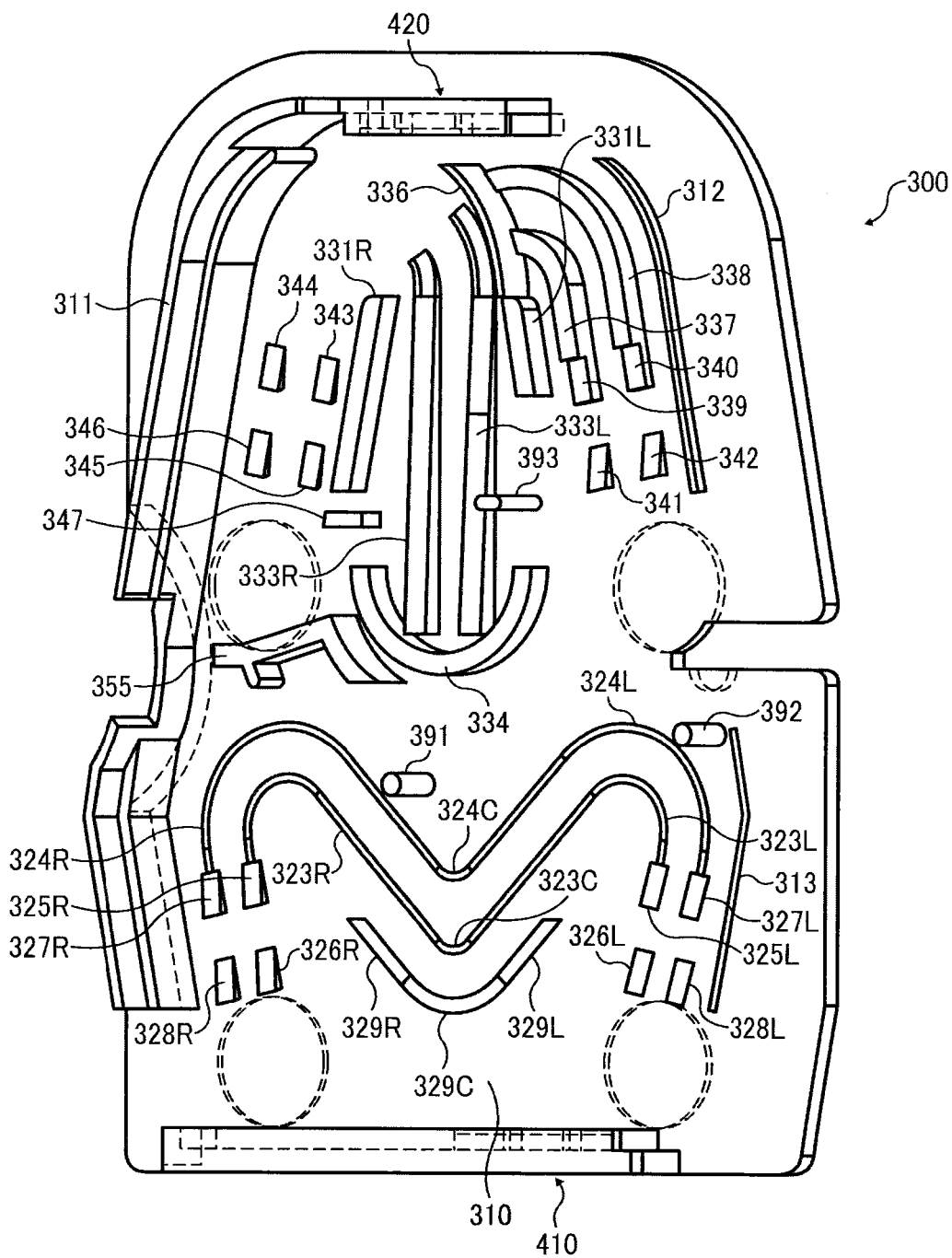
Figure 18B:
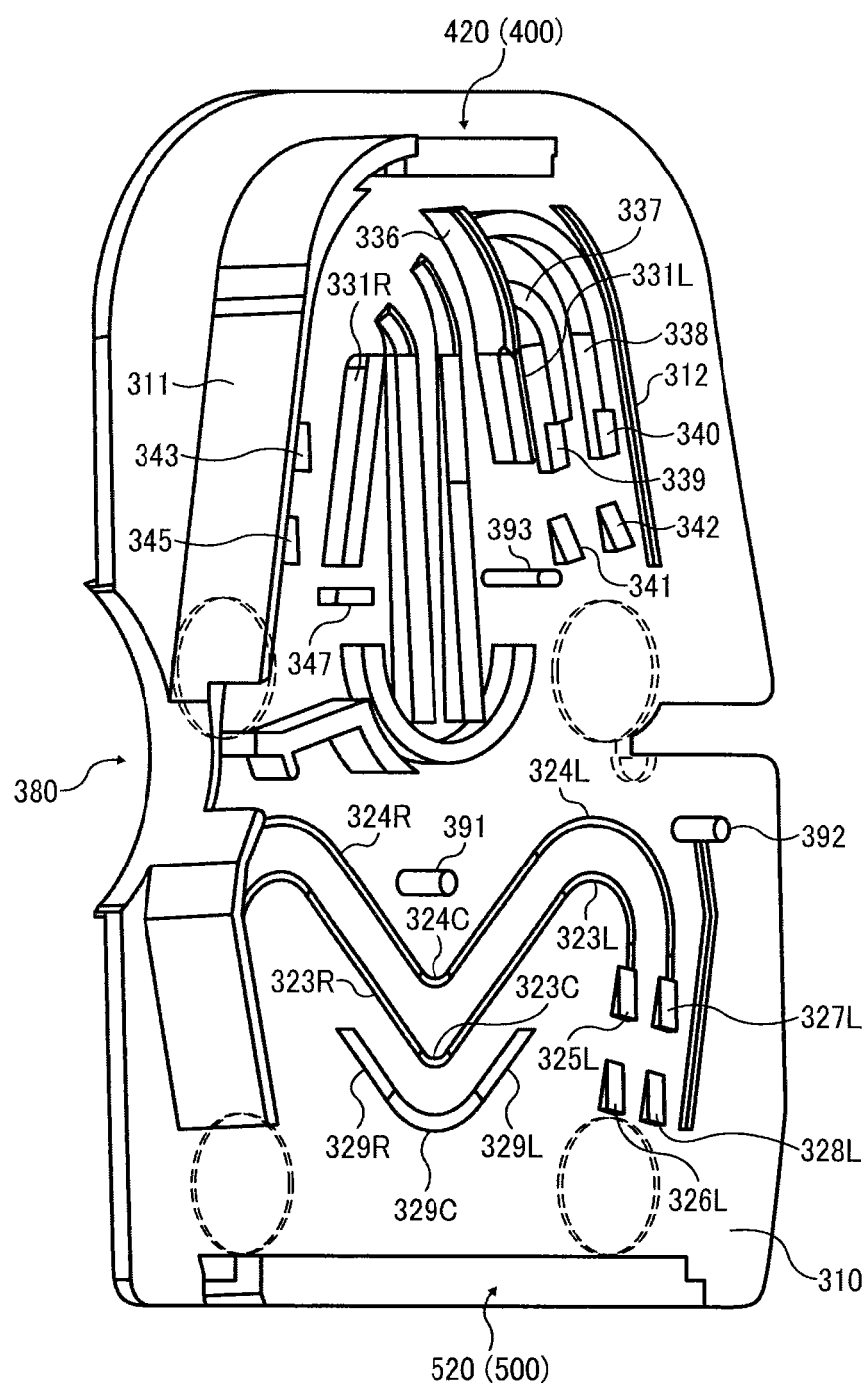

First, the first rear case member 200 will be described. FIGS. 13A and 13B each show the first rear case member of the impact detector, of which FIG. 13A shows a plan view and FIG. 13B shows a bottom view thereof. Similarly, FIGS. 14A and 14B each show the first rear case member of the impact detector, of which FIG. 14A shows a perspective view of the same and FIG. 14B shows a perspective view seen from another direction. FIGS. 15A and 15B each show the second rear case member of the impact detector according to the first embodiment, of which FIG. 15A shows a plan view and FIG. 15B shows a bottom view thereof. Similarly, FIGS. 16A and 16B each show the second rear case member of the impact detector, of which FIG. 15A shows a perspective view of the same and FIG. 15B shows a perspective view seen from another direction. FIGS. 17 and 18 each show the front case of the impact detector, of which FIG. 17A shows a plan view and FIG. 17B shows a bottom view thereof. Similarly, FIGS. 18A and 18B each show the front case of the impact detector, of which FIG. 18A shows a perspective view of the same and FIG. 18B shows a perspective view seen from another direction.

As illustrated in FIGS. 13 and 14, the first rear case member 200 includes a plate-shaped bottom plate 210 and walls 211, 212, and 213 surrounding a periphery of the bottom plate 210. Inside the walls 211, 212, and 213, there are provided partition walls 214R and 214L separating the lateral direction sensor section 180 and the front-back direction sensor section 190.

On the other hand, as illustrated in FIGS. 15A through 16B, the second rear case member 1200 also includes the walls 211, 212, and 213, the lateral direction sensor section 180, the front-back direction sensor section 190, and the partition walls 214R and 214L.

As illustrated in FIGS. 17 and 18, the front case member 300 includes a plate-shaped top plate 310 and a wall 311 built along a partial outline of the top plate 310 (see the right side in FIG. 17A and the left side in FIG. 17B). In addition, the top plate 310 includes two protruded portions 312 and 313. Further, the top plate 310 includes a wall 314 to segment the lateral direction sensor section 180 from the front-back direction sensor section 190 and to support the second weight 130 in the proximal detection position 130F.

Hereinafter, the structure of the first rear case member 200, the second rear case member 1200, and the front case member 300 each forming the lateral direction sensor section 180 will be described, with the first rear case member 200 described first.

The lateral direction sensor section 180 includes, between the first rear case member 200 and the front case member 300, the right-side weight path 140, through which the first weight 120 moves due to the rightward falling, and the left-side weight path 150 through which the first weight 120 moves due to the leftward falling. When the impact detector 100 falls rightward from the initial standing state and returns to the initial standing state, the first weight 120 moves from the initial position 120S to the right-side detection position 120R via the right-side weight path 140, which can be observed from the front case member 300.

Similarly, when the impact detector 100 falls leftward from the initial standing state and returns to the initial standing state, the first weight 120 moves from the initial position 120S to the left-side detection position 120L via the left-side weight path 150, which can be observed from the front case member 300.

First, part of the first rear case member 200 forming the lateral direction sensor section 180 will be described (see FIGS. 13 and 14).

The bottom plate 210 of the first rear case member 200 forming the lateral direction sensor section 180 includes guide projections 221R, 221L and guide projections 222R, 222L which form the right-side weight path 140 and the left-side weight path 150. Herein, suffixes R and L mean 'right' and 'left.' For example, the guide projection 221R shows a right-side guide projection.

The guide projections 221R, 221L are configured to have an interval narrowing downward and connected at a bottom, arc-shaped connecting portion 221C. In the first embodiment, the angle formed between each of the guide projections 221R, 221L and a horizontal line is 45 degrees. As a result, in the lateral direction sensor section 180, the first weight 120 starts to move when the impact detector 100 is slanted in the lateral direction by 45 degrees. The initial position 120S of the first weight 120 is defined at the lowest portion of the guide projections 221R, 221L. The first weight 120 is positioned at the initial position 120S in the initial state in which the impact is not detected. In addition, the guide projections 222R, 222L are formed outside below the guide projections 221R, 221L. The first weight 120 which has moved due to the falling in the lateral direction is held between the right-side detection position 120R or the left-side detection position 120L and a wall 211 (see FIGS. 9A and 9B).

Further, rails 223R, 224R, 223L, and 224L to guide the first weight 120 to the right-side weight path 140 and the left-side weight path 150 while reducing the moving resistance are formed to the bottom plate 210. Cross-sections of the rails 223R, 224R, 223L, and 224L each are formed as a semicircle so that the contact resistance with the first weight 120 is reduced. The rails 223R, 224R, 223L, and 224L are connected via a connection rail 229 disposed vertically. Further, stepped portions 225R, 226R, 225L, and 226L to prevent the first weight 120 held at the right-side detection position 120R or the left-side detection position 120L from moving backward are formed continuously from the rails 223R, 224R, 223L, and 224L.

Further, a contact piece 227 is disposed above the initial position 120S. When the first weight 120 held at the initial position 120S jumps due to a slight shock, the contact piece 227 contacts the first weight 120 to prevent it from moving to the detection position 120R or 120L. As illustrated in FIG. 13A, the contact piece 227 includes a projection 227a formed at the left below the contact piece 227. The projection 227a prevents a malfunction of the first weight 120 due to its jumping by contacting the first weight 120. On the other hand, a recess 227b is formed at the right below the contact piece 227. The recess 227b receives the stopper 391 when the front case member 300 comes into the second combination position (see FIG. 9B). When the stopper 391 enters into the recess 227b, it is configured such that the click feeling is generated.

Next, the second rear case member 1200 will be described (see FIGS. 15A through 16B).

The second rear case member 1200 is constructed substantially similarly to the first rear case member 200 except that the right-side weight path 140 and the left-side weight path 150 are angled at a 60-degree angle relative to the horizontal direction. Accordingly, the difference of the second rear case member 1200 from the first rear case member 200 will be described. As illustrated in FIGS. 15 and 16, the second rear case member 1200 is configured such that guide projections 1221R, 1221L are disposed angled at 60 degrees relative to the horizontal line when the second impact detector 1100 is disposed on the package. The guide projections 1221R, 1221L are disposed such that the interval therebetween is narrowed downward. The initial position 120S of the first weight 120 is defined by the bottom part of the guide projections 1221R, 1221L.

In addition, rails 1228R, 1228L to reduce the moving resistance of the first weight 120 are disposed above the guide projections 1221R, 1221L. The guide projections 1221R, 1221L are joined at the bottom end. Further, disposed is a rail 1229, which extends downward from a joint between the rails 224R, 224L and crosses over a joint between the rails 1228R, 1228L.

Next, a portion constructing the lateral direction sensor section 180 in the front case member 300 will be described (see FIGS. 17A through 18B).

The front case 300 is used in common by both the impact detectors 100 and 1100. Further, rails 323R, 324R, 323L, and 323L to guide the first weight 120 along the right-side weight path 140 and the left-side weight path 150 serving as a resistance reducer to reduce the moving resistance of the first weight 120 are formed on the top plate 310 of the front case member 300. The rails 323R, 324R, 323L, and 323L are connected by arc-shaped members 323C and 324C, respectively. In the first embodiment, the rails 323R and 323L and the arc-shaped portion 323C integrally serve as a second resistance reducer. Further, rails 329R and 329L are disposed, as a resistance reducer, below the arc-shaped portion 323C so as to form a downward convex portion. The rails 329R and 329L are connected by an arc-shaped portion 329C, thereby forming a first resistance reducer. In addition, cross-sections of the rails 323R, 324R, 323L, and 323L, the arc-shaped members 323C and 324C, the rails 329R and 329L, and the arc-shaped portion 329C each are formed as a semicircle, so that the constant resistance is reduced.

Figure 19A:
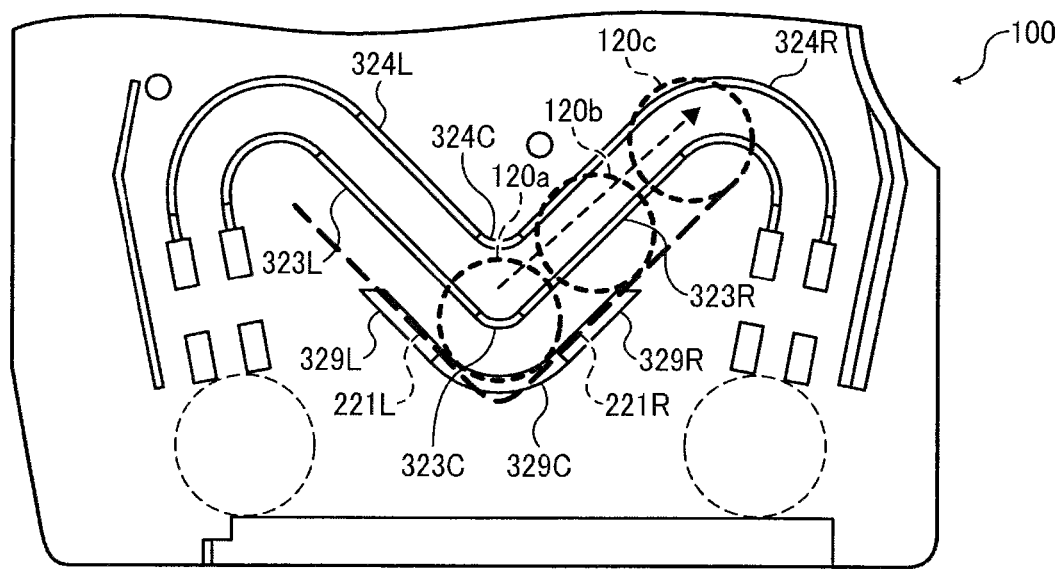
Figure 19B:
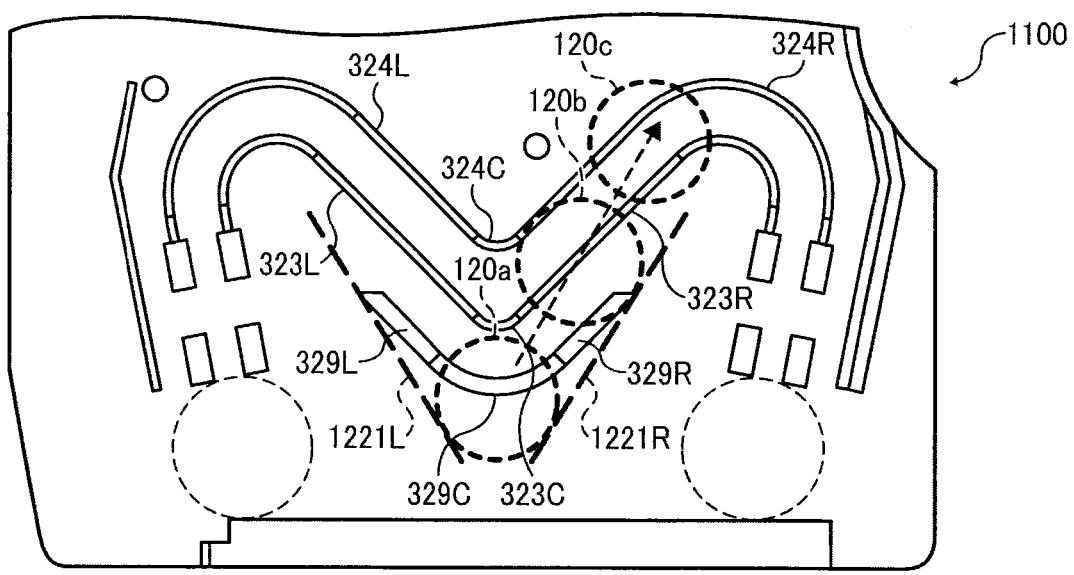
Figure 20:
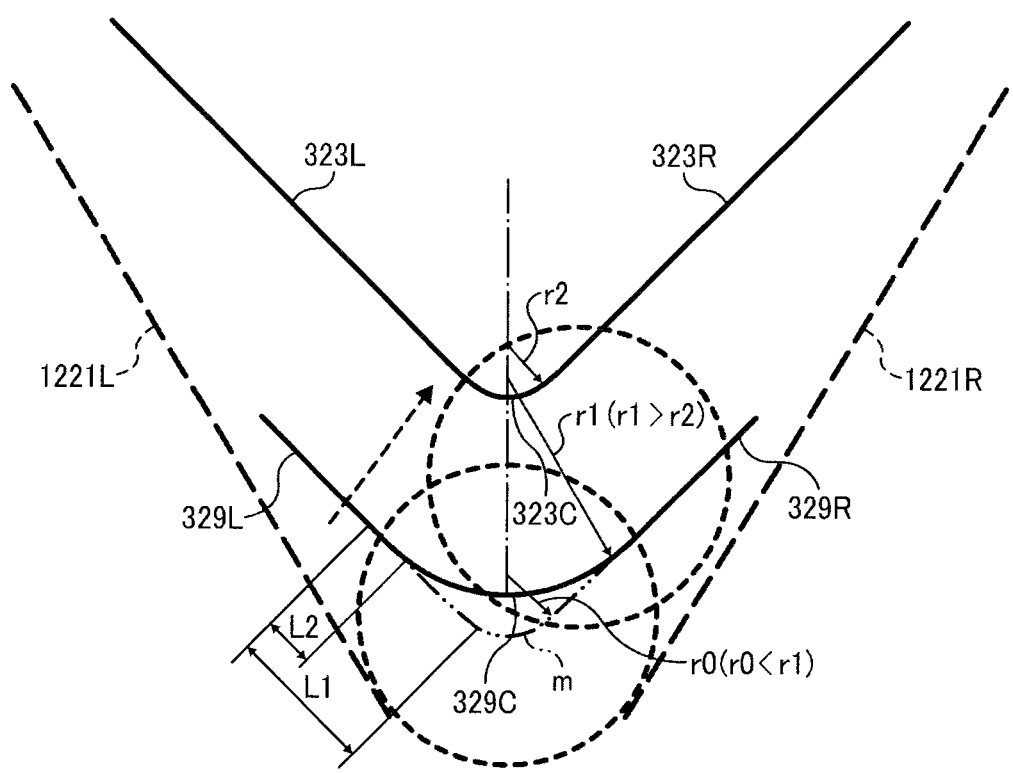
FIG. 20 is a schematic view using the second rear case member of the impact detector showing a contacting state between the rails of the front case and the weight.

A set of the rails 323R and 323L and the arc-shaped portion 323C as a second resistance reducer and a set of the rails 329R and 329L with the arc-shaped portion 329C as a first resistance reducer will be described. FIGS. 19A and 19B each show a contacting state between the rails of the front case and the weight, of which FIG. 19A shows a schematic view using the first rear case member, and FIG. 19B shows a schematic view using the second rear case member. Similarly, FIG. 20 is a schematic view using the second rear case member of the impact detector showing a contacting state between the rails of the front case and the weight.

In the first embodiment, as illustrated in FIG. 19A, when the rails 329R and 329L are combined with the first rear case member 200, the rails 329R and 329L are positioned at the same positions as those of the guide projections 221R, 221L of the first rear case member 200 and are angled at 45 degrees relative to the horizontal line. In addition, the rails 323R and 323L are positioned parallel to the rails 329R and 329L. The interval between the rails 323R and 323L and the rails 329R and 329L is set to smaller than the diameter of the first weight 120.

As illustrated in FIG. 19A, in a state in which the front case member 300 is combined with the first rear case member 200, the first weight 120 moves along the rail 323 while contacting the rails 323R and 324R without contacting the guide projection 221R. In this case, the first weight 120 contacts both the rails 323R and 324R at each position while moving. FIG. 19A shows the first weight 120 while moving from 120a, 120b to 120c, each shown by a broken line. Thus, the first weight 120 does not get hung up on any of the slanted rails. Then, the first weight 120 smoothly moves along the rail 323R.

It is to be noted that the in the first embodiment, an example using the rails is described as a resistance reducer. However, small convex members with a width smaller than that of the rail are disposed regularly, so that another type of resistance reducer may be created.

In addition, as illustrated in FIG. 19B, when the front case member 300 is combined with the second rear case member 1200, when the first weight 120 moves along the rail 323R, the first weight 120 contacts the arc-shaped portion 323C, the arc-shaped portion 329C, the rail 329R, the rail 323R, and the rail 324R, sequentially at two positions. FIG. 19B shows the first weight 120 while moving from 120a, 120b to 120C, each shown by a broken line. Specifically, the first weight 120 contacts the arc-shaped portion 323C and the arc-shaped portion 329C at a position 120a, contacts the rail 323R, the rail 324R, and the rail 329R at a position 120b, and contacts the rail 323R and the rail 324R at a position 120c. As a result, the first weight 120 does not get hung on any of the slanted rails. Accordingly, the first weight 120 smoothly moves along the rail 323R.

In addition, in the first embodiment, as illustrated in FIG. 20, a radius r1 of the arc-shaped portion 329C is greater than a radius r2 of the arc-shaped portion 323C. As a result, the resistance when the first weight 120 moves from the initial position 120S via the guide projections 1221R, 1221L is reduced. Herein, when the radius r1 of the arc-shaped portion 329C is shortened (see line m in FIG. 20 showing an arc-shaped portion when the radius is set to r0), the moving resistance of the first weight 120 increases. This is because, when the first weight 120 moves along a guide projection 1221R, a contact length L1 of the rail 329L when the radius of the first weight 120 is r0 perpendicular to the moving direction of the first weight 120 becomes longer than a length L2 when the radius of first weight 120 is r1.

In addition, the height of the rails 323R and 323L and the arc-shaped portion 323C, the rail 324R and 324L and the arc-shaped portion 324C, and the rails 329R and 329L and the arc-shaped portion 329C is in a range not contacting the first rear case member 200 or the second rear case member 1200 when front case member 300 is slidably constructed with the first rear case member 200 or the second rear case member 1200.

Further, as illustrated in FIGS. 17A through 18B, the top plate 310 of the front case member 300 includes stepped portions 325R, 326R, 327R, 328R, 325L, 326L, 327L, and 328L to prevent the first weight 120 held at the right and left detection positions 120R and 120L from moving backward. The stoppers 391, 392 to prevent the first weight 120 from moving when the first rear case member 200 and the front case member 300 are brought to the first combination position, are disposed in a protruding manner above the initial position 120S. When the first rear case member 200 and the front case member 300 are positioned at the first combination position, the stoppers 391, 392 disposed at the right-side weight path 140 and the left-side weight path 150 prevent the first weight 120 held at the initial position 120S from moving to the detection positions 120R, 120L (see FIG. 6A).

Next, a portion constructing the lateral direction sensor section 180 will be described.

First, an operation to detect falling in the lateral direction by the lateral direction sensor section 180 of the first impact detector 100 will be described.

Figure 21A:
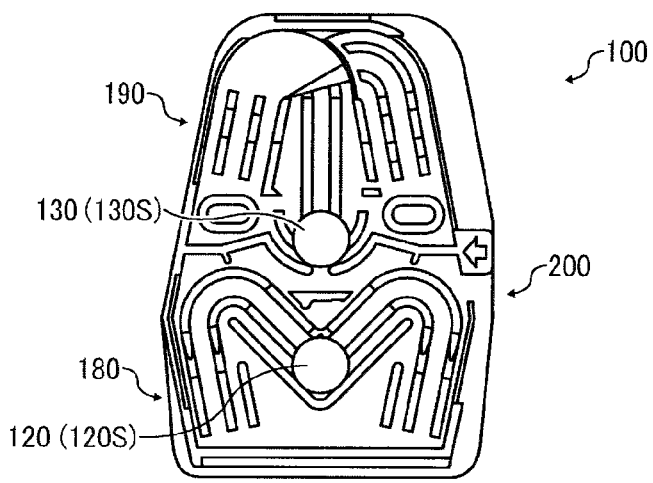
FIGS. 21A to 21C are views each illustrating a state of detecting the impact in the lateral direction when the impact detector employs the first rear case member.
Figure 21B:
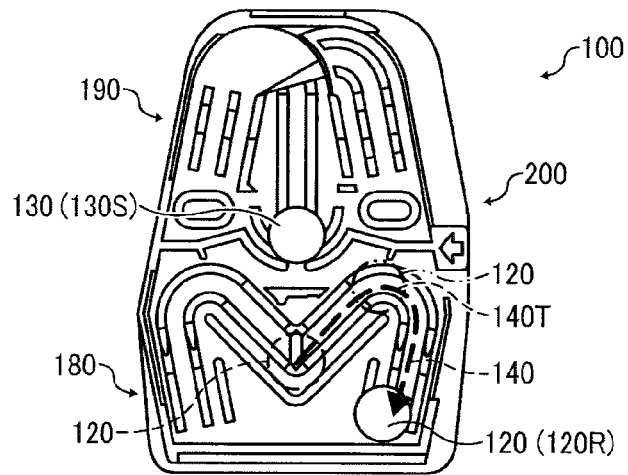
Figure 21C:
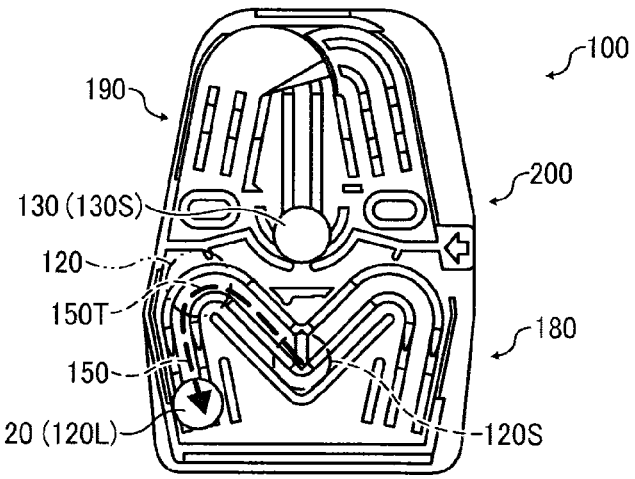

FIGS. 21A-21C are a schematic view illustrating a state of detecting the impact in the lateral direction when the impact detector employs the first rear case member. When the impact detector 100 falls rightward more than a predetermined angle from the directly standing state (see FIG. 21A), the first weight 120 moves along the right-side weight path 140 guided by the rail 323R, 324R, and the arc-shaped members 323C and 324C and reaches a top position 140T of the right-side weight path 140 (see FIGS. 17 and 18). Then, when the impact detector 100 is set back, the first weight 120 moves to the detection position 120R (see FIG. 21B). In this state, the first weight 120 is prevented from moving backward by the stepped portions 225R, 226R of the first rear case member 200 and by the stepped portions 325R, 326R, 327R, and 328R of the front case member 300 and does not return to the right-side weight path 140.

Similarly, when the impact detector 100 falls leftward more than a predetermined angle from the directly standing state (see FIG. 21A), the first weight 120 moves along the left-side weight path 150 guided by the rails 323L, 324L, and the arc-shaped members 323C and 324C so as to reach a top position 150T of the left-side weight path 150 (see FIG. 21C). Then, when the impact detector 100 is set back, the first weight 120 moves to the left-side detection position 120L (see FIG. 21C). In this state, the first weight 120 is prevented from moving backward by the stepped portions 225L, 226L of the first rear case member 200 and by the stepped portions 325L, 326L, 327L, and 328L of the front case member 300 and does not return via the left-side weight path 150.

Next, an operation to detect falling in the lateral direction by the lateral direction sensor section 180 of the second impact detector 1100 will be described.

Figure 22A:
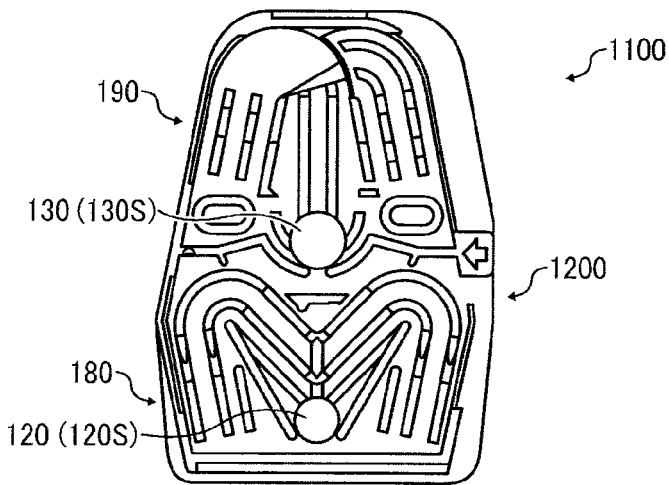
FIGS. 22A to 22C are views each illustrating a state of detecting the impact in the lateral direction when the impact detector employs the second rear case member.
Figure 22B:
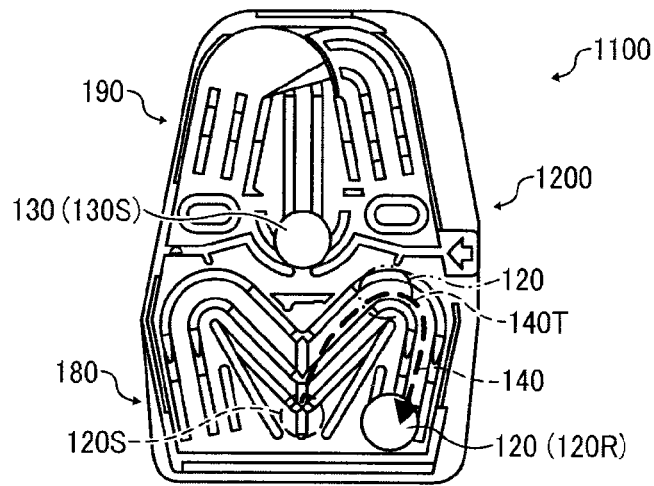
Figure 22C:
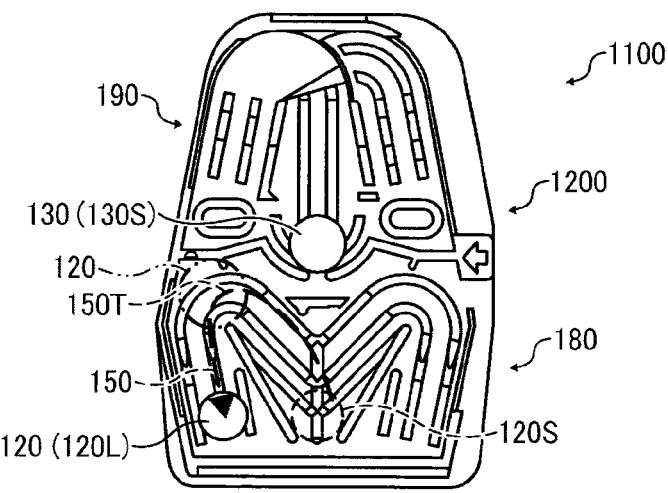

FIGS. 22A-C is a schematic view illustrating a state of detecting the impact in the lateral direction when the impact detector employs the second rear case member according to the first embodiment. When the second impact detector 1100 falls rightward more than a predetermined angle from the directly standing state (see FIG. 22A), the first weight 120 moves along the right-side weight path 140 guided by the arc-shaped portion 329C, the rails 329R, 323R, 324R, the arc-shaped portion 323C, 324C to reach the top position 140T of the right-side weight path 140. Then, when the impact detector 1100 is set back, the first weight 120 moves to the detection position 120R (see FIG. 22B). In this state, the first weight 120 is prevented from moving backward by the stepped portions 225R, 226R of the second rear case member 1200 and the stepped portions 325R, 326R, 327R, and 328R of the front case member 300 and does not return via the right-side weight path 140.

Similarly, when the impact detector 1100 falls leftward more than a predetermined angle from the directly standing state (see FIG. 22A), the first weight 120 moves along the left-side weight path 150 guided by the arc-shaped portion 329C, rail 329L, 323L, 324L, the arc-shaped portions 323C and 324C to reach the top position 150T of the left-side weight path 150. Then, when the impact detector 1100 is set back, the first weight 120 moves to the left-side detection position 120L (see FIG. 22C). In this state, the first weight 120 is prevented from moving backward by the stepped portions 225L, 226L of the second rear case member 1200 and by the stepped portions 325L, 326L, 327L, and 328L of the front case member 300 and does not return via the left-side weight path 150.

Next, the front-back direction sensor section 190 will be described.

The front-back direction sensor section 190 includes, between the first rear case member 200 or the second rear case member 1200 and the front case member 300, the proximal weight path 160 and the distal weight path 170. The second weight 130 moves along the proximal weight path 160 due to the falling toward front and moves along the distal weight path 170 moves due to the falling toward backside. When the first impact detector 100 or the second impact detector 1100 falls toward front from the vertically standing state and then returns to the standing state, the second weight 130 moves from the initial position 130S to the proximal detection position 130F via the proximal weight path 160, which can be observed from the side of the front case member 300.

Similarly, when the impact detector 100 falls backward from the standing posture and then returns to the standing posture, the second weight 130 moves from the initial position 130S to the distal detection position 130B via the distal weight path 170 and can be observed from the front case member 300.

In the first embodiment, because the first rear case member 200 and the second rear case member 1200 each forming the front-back direction sensor section 190 include the same structure, the first rear case member 200 is selected as an example and will be described. Among the first rear case member 200, a portion constructing the front-back direction sensor section 190 will be described (see FIGS. 13 and 14). The bottom plate 210 of the first rear case member 200 forming the front-back direction sensor section 190 includes guide projections 231R and 231L. An arc-shaped hold wall 215, with an upward opening to hold the second weight 130 at the initial position 130S is formed below the guide projections 231R and 231L.

The guide projections 231R and 231L are formed with a slightly increasing interval therebetween in the vertical direction. The initial position 130S of the second weight 130 is defined below the guide projections 231R and 231L (see FIG. 9A) and the second weight 130 is positioned at the initial position 130S in the initial state not sensing any shock or force. In addition, the guide projection 231L includes a malfunction preventing projection 231a to prevent the second weight 130 from jumping due to a vertical shock and moving along the distal weight path 170. In addition, a projection 238 is disposed at a position symmetrical with respect to the malfunction preventing projection 231a so as to prevent the second weight 130 from moving toward the proximal weight path 160 erroneously.

In addition, the partition walls 214R and 214L to hold the second weight 130 which has moved due to the front-back falling are formed outside below the guide projections 231R and 231L. Further, hold projections 235R and 235L are formed on the bottom plate 210 at positions corresponding to the proximal detection position 130F and the distal detection position 130B. The hold projections 235R and 235L prevent fluctuation of the second weight 130. The hold projections 235R and 235L each sandwich the second weight 130 along with the front case member 300.

In addition, rails 232R and 232L to guide the second weight 130 while reducing the moving resistance of the second weight 130 are disposed in an interior of the guide projections 231R and 231L. Further, rails 233R, 233L, 234R, and 234L to guide the second weight 130 are disposed at outer right and left positions. Further, the rails 233R, 233L, 234R, and 234L include stepped portions 241R, 241L, 242R, and 242L to prevent the second weight 130 held at the distal detection position 130B from moving backward.

In addition, above the rails 232R and 232L is formed a curved wall 236 to guide the second weight 130 to move from the initial position 130S to the distal detection position 130B via the distal weight path 170. A gap is formed between an upper end of the curved wall 236 and the front case member 300 and the second weight 130 moving along the proximal weight path 160 passes through the gap. Further, a stepped portion 237, to prevent the backward moving of the second weight 130 held at the distal detection position 130B, is disposed at a beginning of a curved portion 170a in the distal weight path 170.

Next, a portion constructing the front-back direction sensor section 190 among the front case member 300 will be described (see FIGS. 17 and 18).

The top plate 310 of the front case member 300 includes guide projections 331R and 331L to guide the second weight 130 along the proximal weight path 160 and the distal weight path 170. In addition, rails 333R and 333L to guide the second weight 130 while reducing the moving resistance of the second weight 130 are disposed between the guide projections 331R and 331L. Further, an arc-shaped projection 334 to hold the second weight 130 at the initial position 130S is disposed below the rails 333R and 333L. Cross-sections of the rails 333R and 333L each are formed into a semicircle so that the contact resistance with the first weight 120 is reduced.

In addition, the top plate 310 includes a projection 347 to prevent the second weight 130 positioned at the initial position 130S from moving in the second combination position is formed at a position symmetrical with respect to the stopper 393(see FIG. 9A).

Further, the top plate 310 includes a curved wall 336 to guide the second weight 130 moving from the initial position 130S via the proximal weight path 160 to the proximal detection position 130F. A gap is formed between an upper end of the curved wall 336 and the front case member 200, and the second weight 130 moving along the distal weight path 170 passes through the gap.

Rails 337 and 338 to guide the second weight 130 are disposed at positions corresponding to the proximal weight path 160 of the top plate 310. Stepped portions 339 and 340 to prevent the second weight 130 from moving backward are each disposed at a lower end of the rails 337 and 338, respectively. Further, at lower steps of the stepped portions 339 and 340, claws 341 and 342 to prevent the backward moving of the second weight 130 are disposed.

Further, claws 343, 344, 345, and 356 to prevent the backward moving of the second weight 130 from the distal detection position 130B are disposed at positions corresponding to the distal weight path 170 of the top plate 310.

Next, an operation to detect falling in the front-back direction by the front-back direction sensor section 190 of the first impact detector 100 and the second impact detector 1100 will be described. Because the operation of the front-back direction sensor section 190 in the both impact detectors 100 and 1100 is the same, an example using the first impact detector 100 will be described.

Figure 23A:
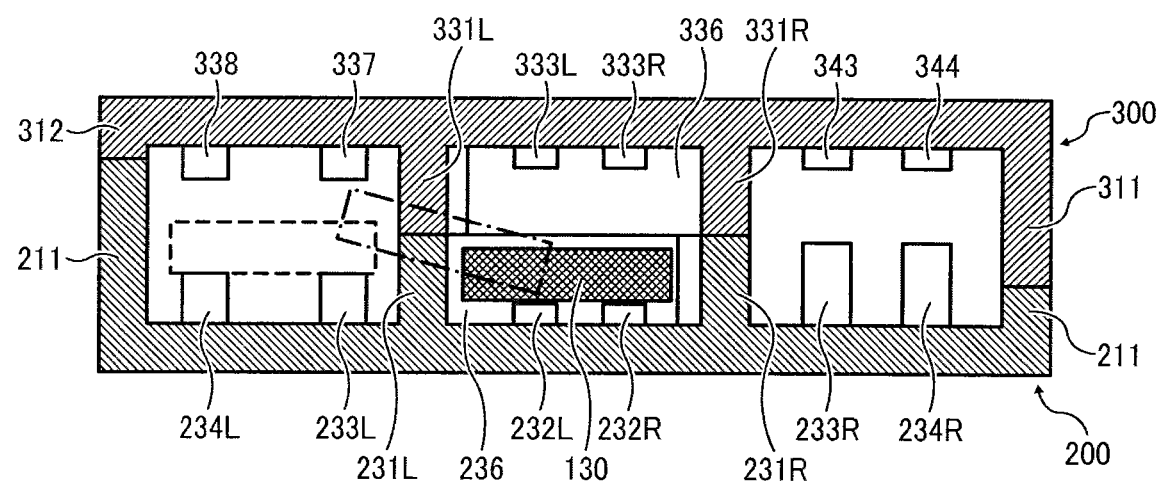
Figure 23B:
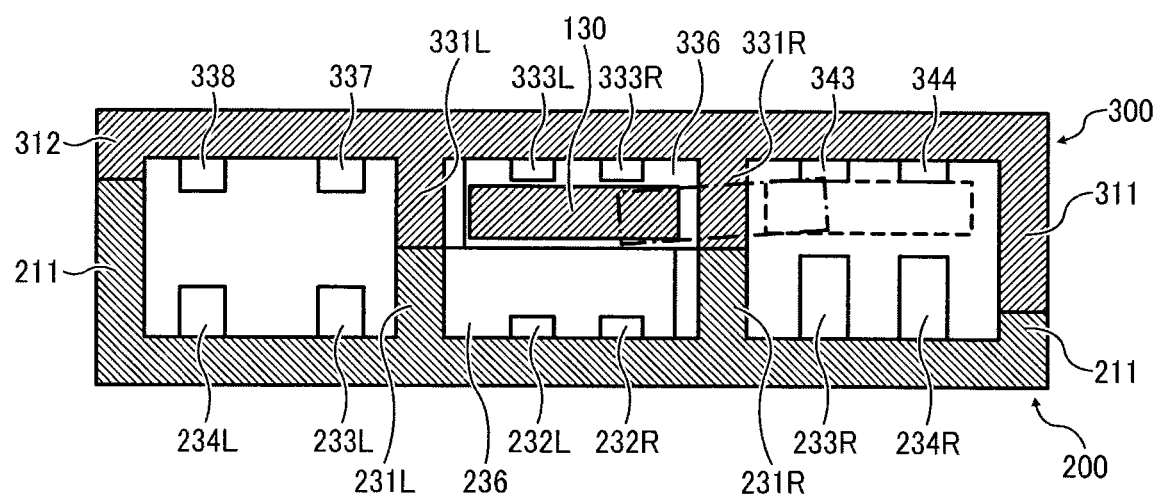
Figure 24A:
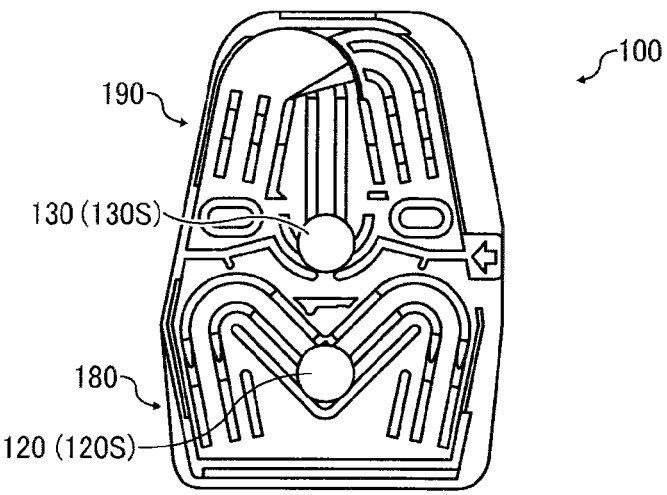
FIGS. 24A to 24C each show a schematic view when the first impact detector detects an impact in the front-back direction.
Figure 24B:
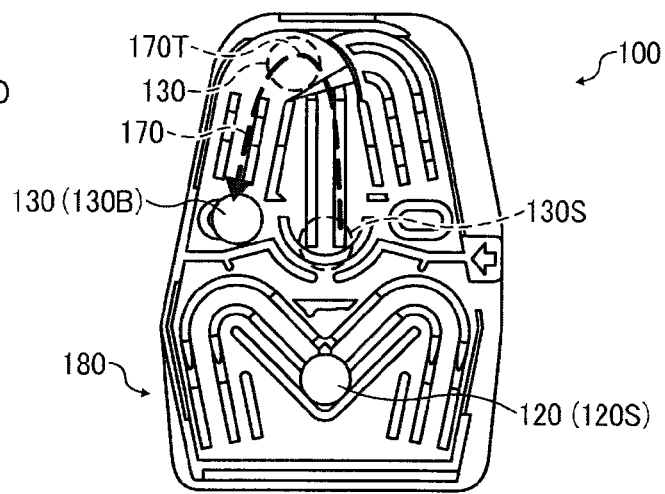
Figure 24C:
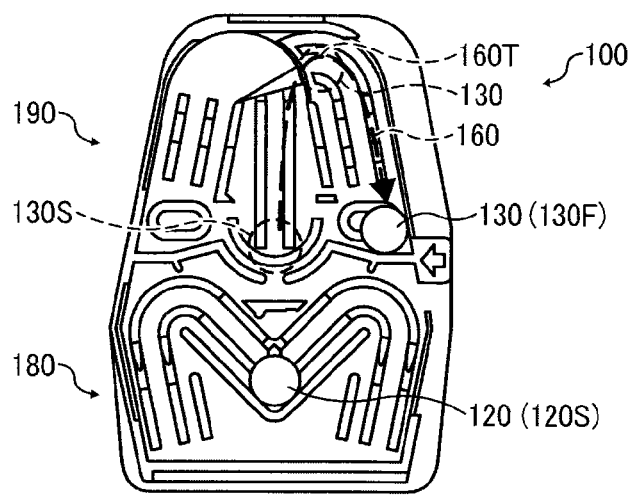

FIGS. 23A and 23B each show a cross-sectional view of the first impact detector 100 along the Line B-B in FIG. 3B, of which FIG. 23A shows a cross-sectional view when the first impact detector 100 falls in the distal direction, and FIG. 23B shows a cross-sectional view when the first impact detector falls in the proximal direction. FIGS. 24A to 24C each show a schematic view when the first impact detector 100 detects an impact in the front-back direction. As illustrated in FIG. 23A, when the impact detector 100 falls backward (that is, toward the first rear case member 200), the second weight 130 slides on the rails 232R and 232L disposed between the guide projections 231R and 231L of the first rear case member 200 and moves up to a peak portion 170T (see FIG. 24B). Next, when the impact detector 100 is brought to the standing state, the second weight 130 slides on the rails 233L and 234L formed between the guide projection 321L and the wall 211, and moves up to the distal detection position 130B. In this case, the second weight 130 crosses over the stepped portion 237.

In this state, moving backward of the second weight 130 positioned at the distal detection position 130B is prevented by stepped portions 241L and 242L, the stepped portions 339 and 340 of the front case member 300, and the claws 341 and 342, so that the second weight 130 does not move backward in the lateral direction sensor section 180.

On the other hand, if the impact detector 100 falls in the frontal direction (that is, toward the front case member 300), the second weight 130 slides on the rails 232R and 232L formed between the guide projections 331R and 331L of the front case member 300 and moves up to a peak portion 160T of the proximal weight path 160 (see FIG. 24C). Next, when the impact detector 100 is brought into a standing state, the second weight 130 passes claws 343 and 344 formed between the guide projection 331R and the wall 211 via the curved wall 336 and is positioned at the proximal detection position 130F. In this state, the second weight 130 is prevented from moving backward by stepped portions 241R and 242 of the first rear case member 200 and claws 343 and 344 of the front case member 300, and does not move backward along the proximal weight path 160.

As a result, the first impact detector 100 and the second impact detector 1100 according to the first embodiment may detect the impact or force due to the turnover in the front-back direction or in the lateral direction. Further, according to the impact detector 100 or 1100, assembly of the product is easier because of a not-complicated structure. In a shippable state of the impact detector 100 or 1100 after the assembly before being attached to the packing, even when an impact or force is applied to the impact detector 100, the impact detector 100 does not come into the impact-detectable state. As a result, handling becomes easier.

In addition, the front case member 300 according to the first embodiment used for the impact detector 100 or 1100 can be used in common for two types of impact detectors detecting two different inclinations. Even used with either of the impact detectors, the front case member 300 can reduce the moving resistance of the weight.

In the first embodiment, the impact detectors 100 and 1100 each including the lateral direction sensor section 180 and the front-back direction sensor section 190 are described as example; however, the impact detector may employ only the lateral direction sensor section. Further, the impact detector may employ other types of sensor sections capable of detecting the impact or force in other directions performed by the lateral direction sensor section and the front-back direction sensor section.

Figure 25:
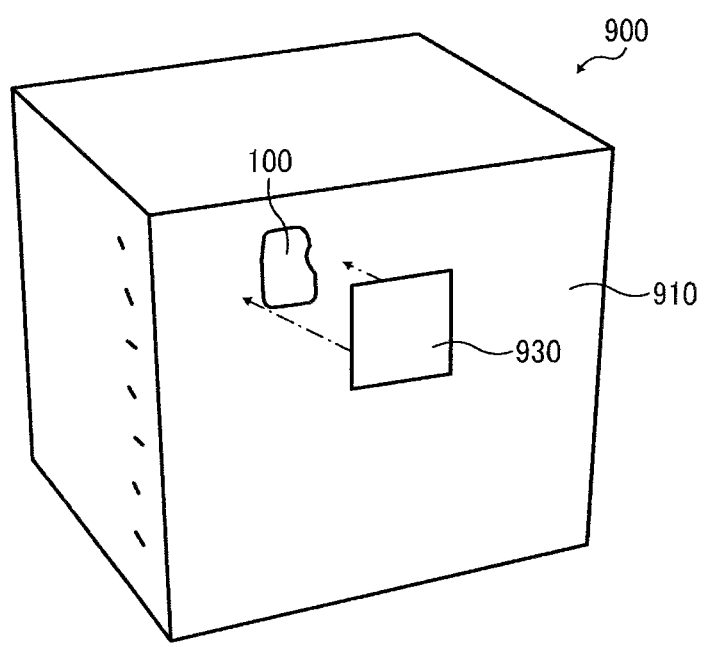
FIG. 25 is a perspective view illustrating a package including an impact detector according to a second embodiment.

Hereinafter, a package including the impact detector according to the first embodiment will be described as a second embodiment. FIG. 25 is a perspective view illustrating a package including a impact detector. In the illustrated example, the first impact detector 100 or the second impact detector 1100 according to the first embodiment is attached to a side 910 of a cardboard box 900 as a detection target using a double-sided adhesive tape and a label 930 is attached thereon. In this case, a combination of the front case member 300 and selected one of the first rear case member 200 and the second rear case member 1200 enables to select the angle for detecting the impact. The impact detector 100 or 1100 may either be attached on the cardboard box 900 or may be fitted in a recess formed on the side 910 of the cardboard box 900 to be fixed on the vertical surface of the shipped product. When the impact detector 100 or 1100 is attached on the cardboard box 900, if the cardboard box 900 falls and receives an impact or force, one may remove the impact detector and remove the front case, so as to return the weight to an initial state (falsification). The label 930 serves as a sealing member. The attached surface of the label 930 should preferably include such an adhesive that a part on the attached surface remains, if removed from the cardboard box 900. Thus, whether or not the seal has been removed for falsification can be checked.

Next, the label 930 will be described.

Figure 26:
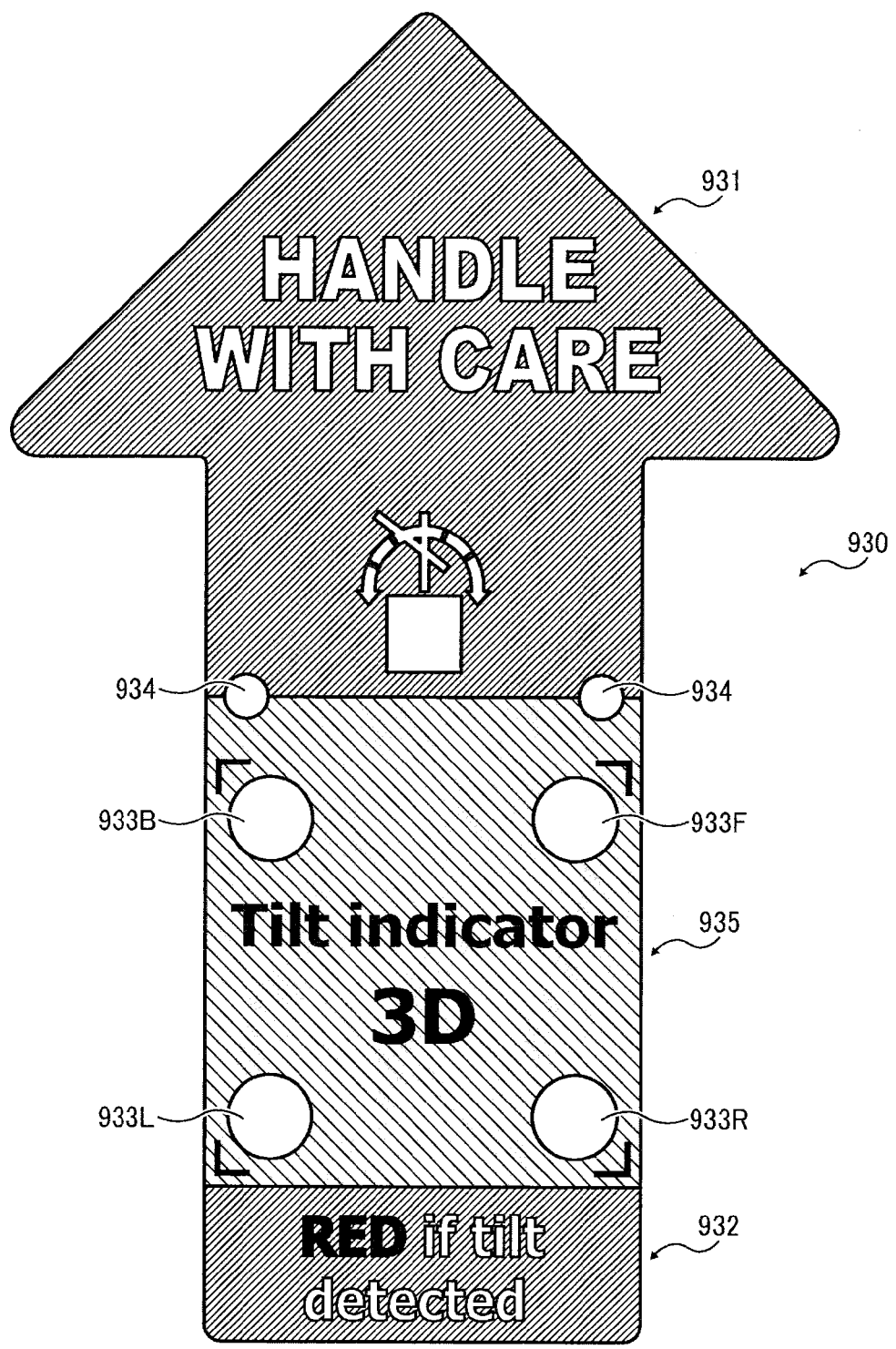
FIG. 26 shows a front view of the label with bottom and side views attached on the front case member.
Figure 27:
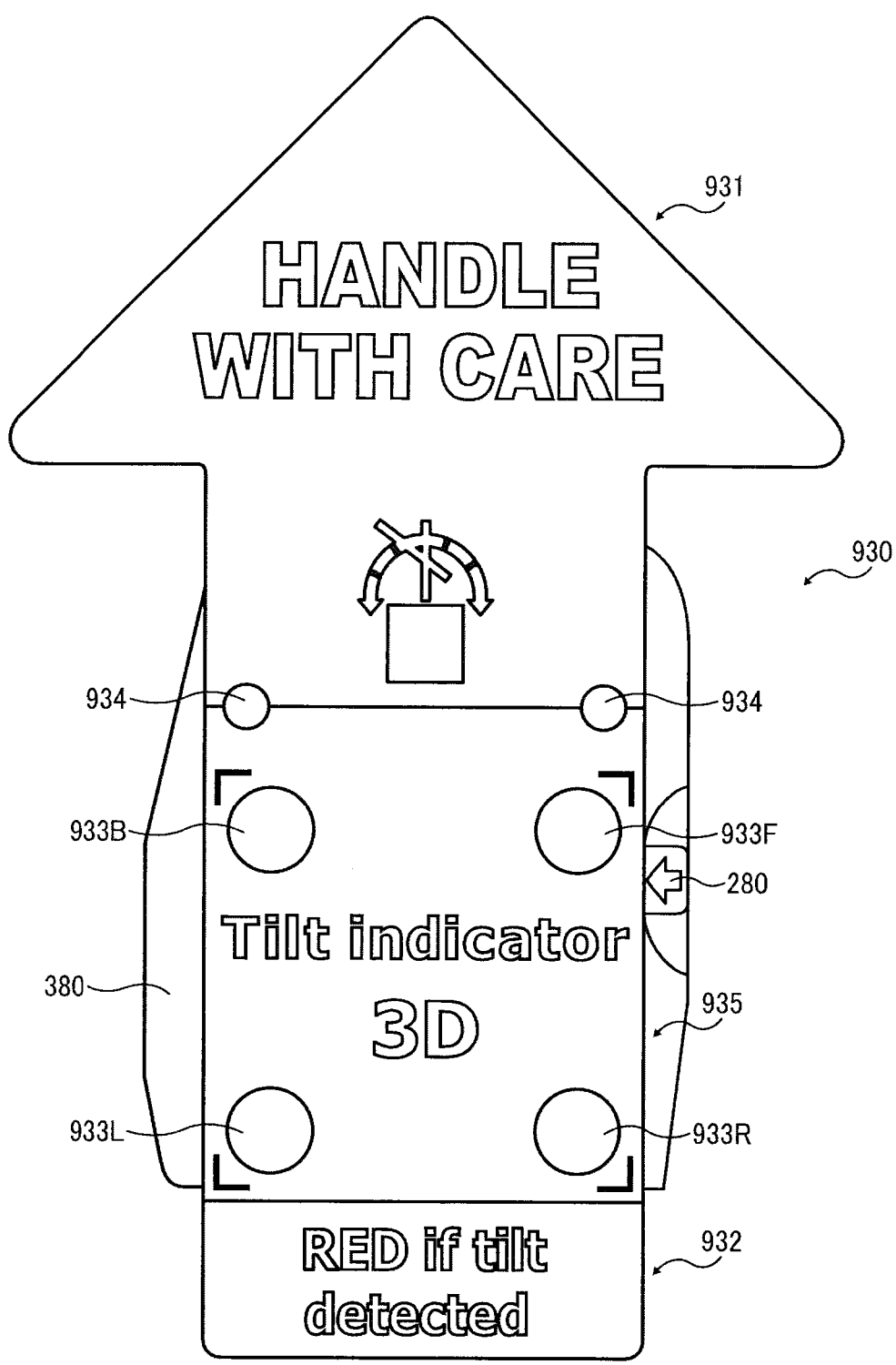
FIG. 27 shows a front view of the label attached on the front case member.

FIG. 26 shows a front view illustrating an example of a label; and FIG. 27 shows a front view of the label attached on the front case member of the impact detector.

Figure 28:
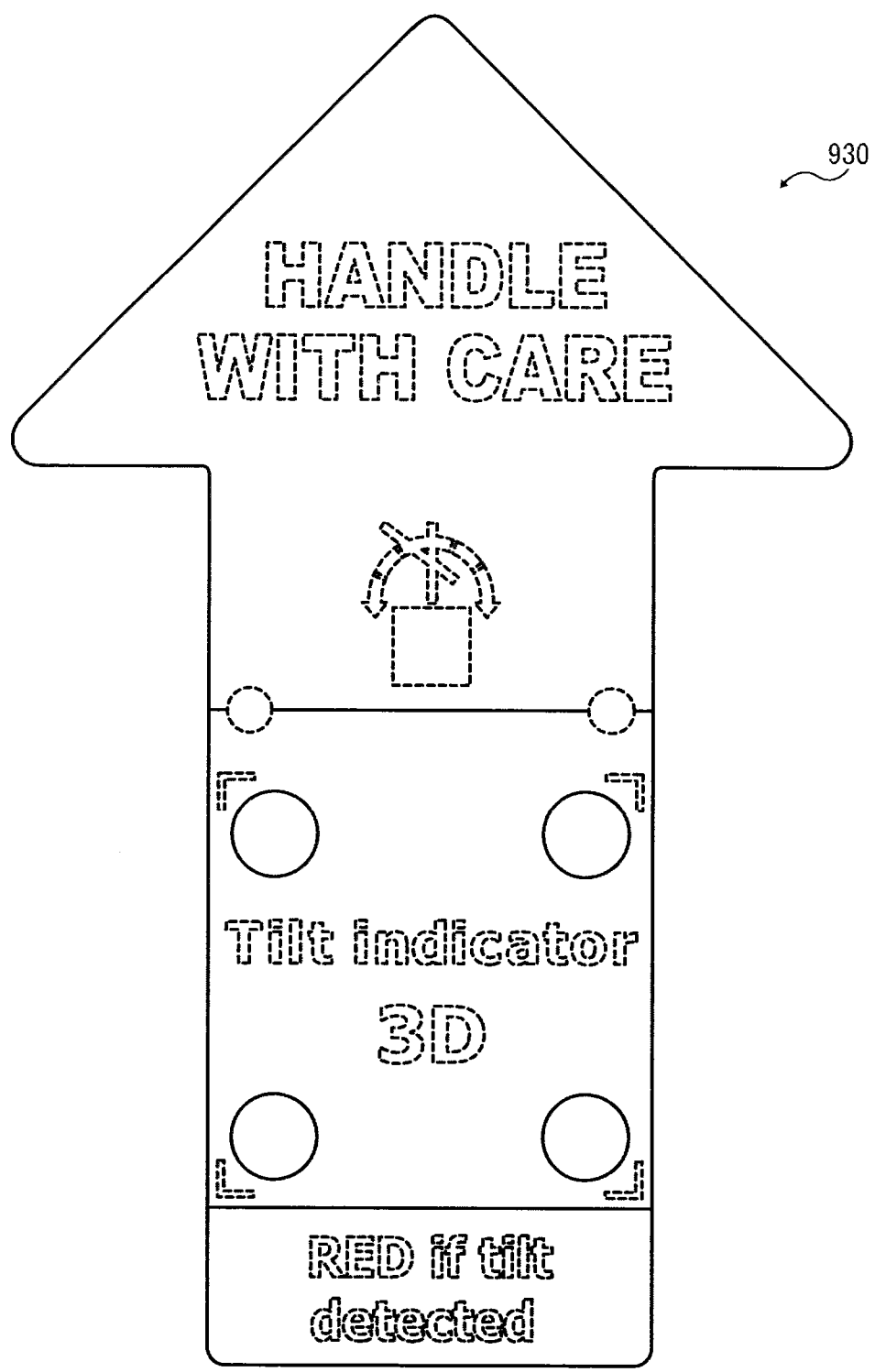
FIG. 28 shows a front view illustrating another example of a label.

As illustrated in FIGS. 26 to 28, the label 930 is formed to have an arrow shape with a tip of the arrow directed upward. FIG. 26 also includes a linear side view of the label 930 seen from the bottom, and a linear longitudinal side view of the label 930 seen from the right side. The label 930 includes three portions, that is, a tip portion 931, a central portion 935, and a bottom portion 932. Background of the tip portion 931 and the bottom portion 932 is black as illustrated by hatched lines rising from left to right, and letters are shown in white. In the present example, the tip portion 931 includes letters of "HANDLE WITH CARE" in white and the bottom portion 932 includes letters "If tilt detected, indicating" in white and a red letter "RED".

The central portion 935 includes displays 933B, 933F, 933L, and 933R, from which the weight can be observed corresponding to positions of the observation windows of the front case member. The display 933B is formed at a position corresponding to the observation window 303, from which the weight moving to the distal detection position 130B is observed. The display 933F is formed at a position corresponding to the observation window 304, from which the weight moving to the proximal detection position 130F is observed. The display 933L is formed at a position corresponding to the observation window 301, from which the weight moving to the left-side detection position 120L is observed. Then, the display 933R is formed at a position corresponding to the observation window 302, from which the weight moving to the right-side detection position 120R is observed.

Further, the color of the central portion 935 should preferably be a complementary color of the color of the weight displayed at the displays 933B, 933F, 933L, and 933R. For example, the central portion 935 is set to yellow (see FIG. 26, in which the central portion 935 is shown by hatched lines falling from left to right). In this case, the color of the weight is set to bluish-purple, which is a complementary color of yellow, so that the visibility of the weight is improved. In addition, the central portion 935 includes letters of "Tilt indicator 3D" represented in black.

In a boundary between the tip portion 931 and the central portion 935, positioning holes 934 are formed. As illustrated in FIG. 27, the positioning holes 934 are provided, for example, so as to easily position the positioning holes 934 at convex portions extending on the surface of the front case member 300. The positioning holes 934 are not necessary if the position to attach the label 930 is conceivable.

Figure 29:
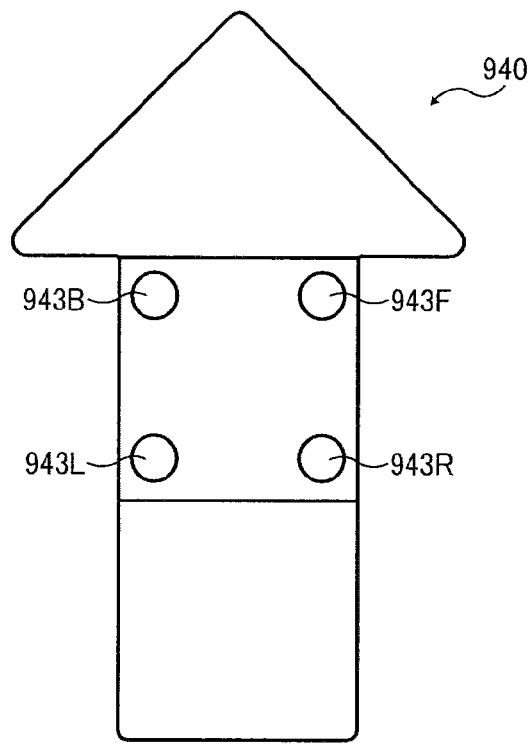
FIG. 29 shows a front view illustrating a modified example of a label.
Figure 30:
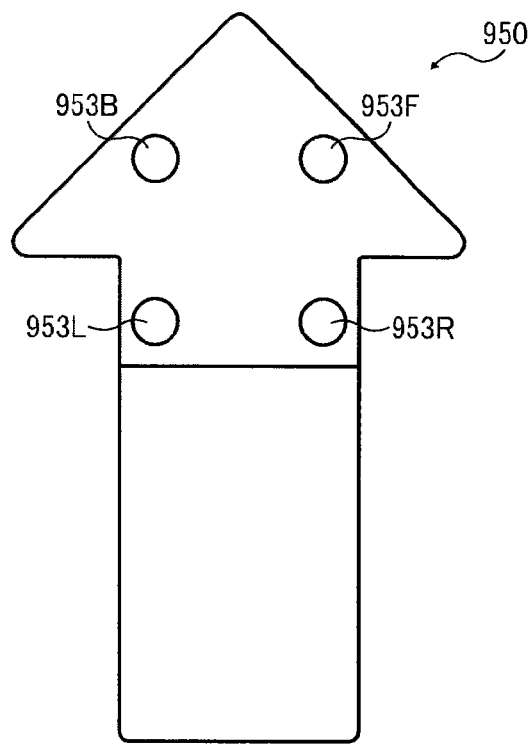
FIG. 30 shows a front view illustrating a modified example of a label.

The positions of the displays 933B, 933F, 933L, and 933R are not limited to the above example. FIG. 29 shows a front view of a modified label; and FIG. 30 shows a front view of another modified label. In a label 940 as illustrated in FIG. 29, displays 943B, 943F, 943L, and 943R are positioned above those of the label 930 in FIG. 28. Further, in a label 950 as illustrated in FIG. 30, displays 953B, 953F, 953L, and 953R are positioned above those of the label 940 in FIG. 29.

Additional modifications and variations of the present invention are possible in light of the above teachings. It is therefore to be understood that, within the scope of the appended claims, the invention may be practiced other than as specifically described herein.

What is claimed is:

1. A case for an impact detector having a weight to move from an initial position when a detection target of the impact detector inclines more than a predetermined angle, comprising:
    a first case to cover a second case including a first guide to guide the weight, or to cover a third case including a second guide to guide the weight and to form a different angle from the first guide; and
    a resistance reducer to reduce moving resistance of the weight, including a first resistance reducer disposed at a same angle as the first guide and a second resistance reducer disposed apart from the first resistance reducer;
    wherein the weight contacts the second resistance reducer when the first case is attached to the second case; and the weight contacts the first resistance reducer and the second resistance reducer when the first case is attached to the third case.

2. The case for the impact detector as claimed in claim 1, wherein the second resistance reducer is disposed parallel to the first resistance reducer.

3. The case for the impact detector as claimed in claim 1, wherein each of the first resistance reducer and the second resistance reducer includes:
    rails extending from a position corresponding to the initial position of the weight symmetrically toward lateral sides along either guide; and
    an arc-shaped connection portion protruding in the direction that intersects the moving direction of the weight,
    wherein a radius of the arc-shaped connection portion of the first resistance reducer is greater than a radius of the arc-shaped connection portion of the second resistance reducer.

4. An impact detector comprising:
    a first case as claimed in claim 1;
    at least one of a second case and a third case as claimed in claim 1; and
    a weight.

5. The impact detector as claimed in claim 4, wherein the second and the third cases are assembled by sliding, and the first resistance reducer and the second reducer have a height not disturbing the second and the third cases while being slidably assembled.

6. A package including a product, comprising:
an impact detector as claimed in claim 4, attached to at least one side of the package.

7. An impact detector, comprising:
a case;
a weight to move from an initial position when a detection target of the impact detector inclines more than a predetermined angle;
a cover of the case, including a guide to guide the weight; and
a resistance reducer to reduce moving resistance of the weight, including a first resistance reducer to form a different angle from the guide and a second resistance reducer disposed apart from the first resistance reducer;
wherein the weight contacts the first resistance reducer and the second resistance reducer when the case is attached to the cover.

* * * * *